United States Patent
Park et al.

(10) Patent No.: US 10,626,397 B2
(45) Date of Patent: Apr. 21, 2020

(54) THERAPEUTIC COMPOSITIONS FOR BREAST CANCER CONTAINING PROTEIN KINASE D1 INHIBITOR

(71) Applicant: SOOKMYUNG WOMEN'S UNIVERSITY INDUSTRY ACADEMIC COOPERATION FOUNDATION, Seoul (KR)

(72) Inventors: Jong Hoon Park, Seoul (KR); Do Yeon Kim, Seoul (KR); Eun Young Park, Seoul (KR); Kyung-Hee Chun, Seoul (KR); Eun Ji Lee, Seoul (KR); Eun Sun Chang, Seoul (KR); Hyeok-Gu Kang, Seoul (KR)

(73) Assignee: SOOKMYUNG WOMEN'S UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 172 days.

(21) Appl. No.: 15/617,788

(22) Filed: Jun. 8, 2017

(65) Prior Publication Data

US 2017/0369887 A1    Dec. 28, 2017

(30) Foreign Application Priority Data

Jun. 8, 2016 (KR) .................. 10-2016-0071126
Jun. 8, 2017 (KR) .................. 10-2017-0071824

(51) Int. Cl.
    *A61K 48/00*        (2006.01)
    *C12N 15/11*        (2006.01)
    (Continued)

(52) U.S. Cl.
    CPC ........ *C12N 15/1137* (2013.01); *C12Q 1/6886* (2013.01); *C12Y 207/11013* (2013.01);
    (Continued)

(58) Field of Classification Search
    CPC .......... C12N 15/1137; C12N 2310/141; C12Y 207/11013; G01N 33/57415; C12Q 2600/158
    See application file for complete search history.

(56) References Cited

U.S. PATENT DOCUMENTS

2004/0180848 A1 * 9/2004 Fesik .................. C12N 15/113
                                                               514/44 A

FOREIGN PATENT DOCUMENTS

WO    WO 2009/099991    *   2/2009
WO    WO 2009/147246 A1 *   6/2009

OTHER PUBLICATIONS

Kim et al. (Oncotarget, 2016 vol. 7:14791-14802).*

(Continued)

*Primary Examiner* — Terra C Gibbs
(74) *Attorney, Agent, or Firm* — Novick, Kim & Lee, PLLC; Jae Youn Kim

(57) ABSTRACT

A method of inhibiting the growth of cancer stem cells, including administering an effective amount of a protein kinase D1 expression or activity inhibitor as an active ingredient to a subject having cancer is provided. Further, a method of treating cancer, including administering an effective amount of a protein kinase D1 expression or activity inhibitor, and antitumor agent as active ingredients to a subject having cancer is provided. Further, a method for measuring expression or activity of protein kinase D1 for providing information of breast cancer prognosis, including a step of measuring expression or activity of protein kinase D1 in cells or tissues isolated from a subject is provided.

9 Claims, 30 Drawing Sheets

Specification includes a Sequence Listing.

(51) Int. Cl.
    C07H 21/02    (2006.01)
    C07H 21/04    (2006.01)
    C12N 15/113   (2010.01)
    G01N 33/574   (2006.01)
    C12Q 1/6886   (2018.01)
(52) U.S. Cl.
    CPC . G01N 33/57415 (2013.01); *C12N 2310/141* (2013.01); *C12Q 2600/158* (2013.01); *G01N 2333/912* (2013.01)

(56) References Cited

OTHER PUBLICATIONS

No Two Cancers are the Same. Cancer Research Wales, https://www.cancerresearchwales.co.uk/blog/no-two-cancers-are-the-same, downloaded on Jul. 3, 2019.*
Sundram et al. (Mol Cancer Res. Aug. 2011; 9(8): 985-996).*
Rozengurt et al. (Journal of Biological Chemistry, vol. 280, No. 14, Issue of Apr. 8, pp. 13205-13208, 2005).*
Cui J et al., MiR-873 Regulates ERα Transcriptional Activity and Tamoxifen Resistance via Targeting CDK3 in Breast Cancer Cells, Chemistry Faculty Publications, Oncogene (2014), pp. 1-13, Macmillan Publishers Limited.
Chaffer CL, Weinberg RA, A Perspective on Cancer Cell Metastasis, Science, Mar. 25, 2011, p. 1559-1564, vol. 331, American Association for the Advancement of Science, Washington, DC.
Li Laisheng et al., MiR-34a inhibits proliferation and migration of breast cancer through down-regulation of Bcl-2 and SIRT1, Clinical and experimental medicine. (2013) 13, pp. 109-117, Springer-Verlag 2012.
Visvader JE, Lindeman GJ, Cancer stem cells in solid tumours: accumulating evidence and unresolved questions, Nat. Rev. Cancer, Oct. 2008, pp. 755-768, vol. 8, Macmillan Publishers Limited.
Park EY et al., Targeting of miR34a-NOTCH1 Axis Reduced Breast Cancer Stemness and Chemoresistance, Cancer research; 74(24), Dec. 15, 2014, pp. 7573-7582, American Association for Cancer Research.
Liu S et al., Role of microRNAs in the Regulation of Breast Cancer Stem Cells, Journal of Mammary Gland Biology and Neoplasia (2012) 17, pp. 15-21, Springer Science+Business Media, LLC.
Schwarzenbacher D et al., The Role of MicroRNAs in Breast Cancer Stem Cells, International Journal of Molecular Sciences 2013, 14, pp. 14712-14723.
Yu F et al., MicroRNA 34c Gene Down-regulation via DNA Methylation Promotes Self-renewal and Epithelial-Mesenchymal Transition in Breast Tumor-initiating Cells, The Journal of Biological Chemistry, Jan. 2, 2012, pp. 465-473, vol. 287, No. 1, The American Society for Biochemistry and Molecular Biology, Inc., U.S.A.
Fu Y, Rubin, CS., Protein kinase D: coupling extracellular stimuli to the regulation of cell physiology, EMBO reports 2011, pp. 785-796, vol. 12, No. 8, European Molecular Biology Organization.
Iglesias T et al., Identification of in Vivo Phosphorylation Sites Required for Protein Kinase D Activation*, The Journal of biological chemistry, Issue of Oct. 16, 1998, pp. 27662-27667, vol. 273, No. 42, The American Society for Biochemistry and Molecular Biology, Inc., U.S.A.
Valverde AM. et al., Molecular cloning and characterization of protein kinase D: A target for diacylglycerol and phorbol esters with a distinctive catalytic domain, Biochemistry, Proceedings of the National Academy of Sciences of the United States of America, Aug. 1994, pp. 8572-8576, vol. 91.
Rozengurt E et al., Protein Kinase D Signaling*, Minireview, The Journal of biological chemistry, Issue of Apr. 8 2005, pp. 13205-13208, vol. 280, No. 14, The American Society for Biochemistry and Molecular Biology, Inc., U.S.A.
Jacamo R et al., Sequential Protein Kinase C (PKC)-dependent and PKC-independent Protein Kinase D Catalytic Activation via Gq-coupled Receptors Differential REGULATIONOFACTIVATIONLOOPSER744ANDSER748 Phosphorylation*, The Journal of Biological Chemistry, May 9, 2008, pp. 12877-12887, vol. 283, No. 19, The American Society for Biochemistry and Molecular Biology, Inc., U.S.A.
Storz P et al., Protein Kinase D mediates a stress-induced NF-kB activation and survival pathway, The EMBO journal 2003, pp. 109-120, vol. 22 No. 1.
Sinnett-Smith J et al., Protein Kinase D Potentiates DNA Synthesis Induced by Gq-coupled Receptors by Increasing the Duration of ERK Signaling in Swiss 3T3 Cells*, The Journal of biological chemistry Issue of Apr. 16, 2004, pp. 16883-16893, vol. 279, No. 16, The American Society for Biochemistry and Molecular Biology, Inc., U.S.A.
Harikumar KB et al., A Novel Small-Molecule Inhibitor of Protein Kinase D Blocks Pancreatic Cancer Growth In vitro and In vivo, Research Article, Molecular cancer therapeutics; 9(5) May 2010, pp. 1136-1146, American Association for Cancer Research.
Misso G et al., Therapeutic Aptamers March On, Molecular therapy-Nucleic acids (2014) 3, e194, The American Society of Gene & Cell Therapy.
Achari C et al., Expression of miR-34c induces G2/M cell cycle arrest in breast cancer cells, Research Article, BMC cancer 2014, 14:538, pp. 1-9, BioMed Central Ltd.
Kato M et al., The mir-34 microRNA is required for the DNA damage response in vivo in C. elegans and in vitro in human breast cancer cells, Oncogene (2009) 28, pp. 2419-2424, Macmillan Publishers Limited.
Du C et al., Protein Kinase D1-Mediated Phosphorylation and Subcellular Localization of B-Catenin, Research Article, Cancer research Feb. 1, 2009, 2009; 69: (3), pp. 1117-1124, American Association for Cancer Research.
Jope RS et al., Glycogen Synthase Kinase-3 (GSK3): Inflammation, Diseases, and Therapeutics, Neurochemical Research (2007) 32, pp. 577-595, Springer Science+Business Media, Inc.
Yuan J et al., Protein kinase D regulates cell death pathways in experimental pancreatitis, Original Research Article, Mar. 27, 2012, pp. 1-17, vol. 3 Art. 60, Gastrointestinal Sciences, Frontiers in Physiology.
Jaggi M et al., Protein kinase D1: A Protein of emerging translational interest, Article in Frontiers in bioscience 12, May 1, 2007, pp. 3757-3767.
Sundram V et al., Emerging Roles of Protein Kinase D1 in Cancer, Subject Review, Molecular Cancer Research 9 (8), Aug. 2011, pp. 985-996, American Association for Cancer Research.
Eiseler T et al., Protein kinase D1 regulates matrix metalloproteinase expression and inhibits breast cancer cell invasion, Research article, Breast cancer research 2009, pp. 1-12, vol. 11 No. 1, BioMed Central Ltd.
Bowden ET et al., An invasion-related complex of cortactin, paxillin and PKCm associates with invadopodia at sites of extracellular matrix degradation, Complex of cortactin, paxillin and PKCm in invadopodia, Oncogene 1999; 18, pp. 4440-4449, Stockton Press.
Borges S et al., Pharmacologic reversion of epigenetic silencing of the PRKD1 promoter blocks breast tumor cell invasion and metastasis, Breast cancer research 2013, 15:R66, pp. 1-15, BioMed Central Ltd.
Liu C et al., The microRNA miR-34a inhibits prostate cancer stem cells and metastasis by directly repressing CD44, Nature medicine, Feb. 2011, pp. 211-215, vol. 17 No. 2, Nature America, Inc.
Nallas D et al., Targeting Epigenetic Regulation of miR-34a for Treatment of Pancreatic Cancer by Inhibition of Pancreatic Cancer Stem Cells, PLoS one, Aug. 2011, pp. 1-12, vol. 6 Issue 8 e24099.
Stankevicins L et al., MiR-34a is up-regulated in response to low dose, low energy X-ray induced DNA damage in breast cells, Radiation oncology 2013; 8:231, pp. 1-8, BioMed Central Ltd.
Guessous F et al., microRNA-34a is tumor suppressive in brain tumors and glioma stem cells, Cell cycle, Mar. 15, 2010, pp. 1031-1036, vol. 9 Issue 6, Landes Bioscience.

(56) References Cited

OTHER PUBLICATIONS

Jaggi M et al., E-Cadherin Phosphorylation by Protein Kinase D1/Protein Kinase CM is Associated with Altered Cellular Aggregation and Motility in Prostate Cancer, Research Article, Cancer research 2005; 65: (2). Jan. 15, 2005, pp. 483-492, American Association for Cancer Research.

Ciani L, Salinas PC, WNTS in the Vertebrate Nervous System: From Patterning to Neuronal Connectivity, Nat Rev Neurosci., May 2005; pp. 351-362, vol. 6, Nature Publishing Group.

Kroon J et al., Glycogen synthase kinase-3β inhibition depletes the population of prostate cancer stem/progenitor-like cells and attenuates metastatic growth, Oncotarget, Dec. 5, 2013, pp. 8986-8994, 2014, vol. 5, No. 19.

\* cited by examiner

SEQUENCE LISTING

```
<160> NUMBER OF SEQ ID NOS: 4

<210> SEQ ID NO 1
<211> LENGTH: 912
<212> TYPE: PRT
<213> ORGANISM: Homo sapiens

<400> SEQUENCE: 1

Met Ser Ala Pro Pro Val Leu Arg Pro Pro Ser Pro Leu Leu Pro Val
1               5                   10                  15

Ala Ala Ala Ala Ala Ala Ala Ala Ala Leu Val Pro Gly Ser Gly
            20                  25                  30

Pro Gly Pro Ala Pro Phe Leu Ala Pro Val Ala Ala Pro Val Gly Gly
        35                  40                  45

Ile Ser Phe His Leu Gln Ile Gly Leu Ser Arg Glu Pro Val Leu Leu
    50                  55                  60

Leu Gln Asp Ser Ser Gly Asp Tyr Ser Leu Ala His Val Arg Glu Met
65                  70                  75                  80

Ala Cys Ser Ile Val Asp Gln Lys Phe Pro Glu Cys Gly Phe Tyr Gly
                85                  90                  95

Met Tyr Asp Lys Ile Leu Leu Phe Arg His Asp Pro Thr Ser Glu Asn
            100                 105                 110

Ile Leu Gln Leu Val Lys Ala Ala Ser Asp Ile Gln Glu Gly Asp Leu
        115                 120                 125

Ile Glu Val Val Leu Ser Ala Ser Ala Thr Phe Glu Asp Phe Gln Ile
    130                 135                 140

Arg Pro His Ala Leu Phe Val His Ser Tyr Arg Ala Pro Ala Phe Cys
145                 150                 155                 160

Asp His Cys Gly Glu Met Leu Trp Gly Leu Val Arg Gln Gly Leu Lys
                165                 170                 175

Cys Glu Gly Cys Gly Leu Asn Tyr His Lys Arg Cys Ala Phe Lys Ile
            180                 185                 190

Pro Asn Asn Cys Ser Gly Val Arg Arg Arg Leu Ser Asn Val Ser
        195                 200                 205

Leu Thr Gly Val Ser Thr Ile Arg Thr Ser Ser Ala Glu Leu Ser Thr
    210                 215                 220
```

-continued

Ser Ala Pro Asp Glu Pro Leu Leu Gln Lys Ser Pro Ser Glu Ser Phe
225                 230                 235                 240

Ile Gly Arg Glu Lys Arg Ser Asn Ser Gln Ser Tyr Ile Gly Arg Pro
            245                 250                 255

Ile His Leu Asp Lys Ile Leu Met Ser Lys Val Lys Val Pro His Thr
            260                 265                 270

Phe Val Ile His Ser Tyr Thr Arg Pro Thr Val Cys Gln Tyr Cys Lys
        275                 280                 285

Lys Leu Leu Lys Gly Leu Phe Arg Gln Gly Leu Gln Cys Lys Asp Cys
    290                 295                 300

Arg Phe Asn Cys His Lys Arg Cys Ala Pro Lys Val Pro Asn Asn Cys
305                 310                 315                 320

Leu Gly Glu Val Thr Ile Asn Gly Asp Leu Leu Ser Pro Gly Ala Glu
                325                 330                 335

Ser Asp Val Val Met Glu Glu Gly Ser Asp Asp Asn Asp Ser Glu Arg
            340                 345                 350

Asn Ser Gly Leu Met Asp Asp Met Glu Glu Ala Met Val Gln Asp Ala
        355                 360                 365

Glu Met Ala Met Ala Glu Cys Gln Asn Asp Ser Gly Glu Met Gln Asp
370                 375                 380

Pro Asp Pro Asp His Glu Asp Ala Asn Arg Thr Ile Ser Pro Ser Thr
385                 390                 395                 400

Ser Asn Asn Ile Pro Leu Met Arg Val Val Gln Ser Val Lys His Thr
                405                 410                 415

Lys Arg Lys Ser Ser Thr Val Met Lys Glu Gly Trp Met Val His Tyr
            420                 425                 430

Thr Ser Lys Asp Thr Leu Arg Lys Arg His Tyr Trp Arg Leu Asp Ser
        435                 440                 445

Lys Cys Ile Thr Leu Phe Gln Asn Asp Thr Gly Ser Arg Tyr Tyr Lys
    450                 455                 460

Glu Ile Pro Leu Ser Glu Ile Leu Ser Leu Glu Pro Val Lys Thr Ser
465                 470                 475                 480

Ala Leu Ile Pro Asn Gly Ala Asn Pro His Cys Phe Glu Ile Thr Thr
                485                 490                 495

Ala Asn Val Val Tyr Tyr Val Gly Glu Asn Val Val Asn Pro Ser Ser
            500                 505                 510

Pro Ser Pro Asn Asn Ser Val Leu Thr Ser Gly Val Gly Ala Asp Val
        515                 520                 525

Ala Arg Met Trp Glu Ile Ala Ile Gln His Ala Leu Met Pro Val Ile
530                 535                 540

Pro Lys Gly Ser Ser Val Gly Thr Gly Thr Asn Leu His Arg Asp Ile
545                 550                 555                 560

Ser Val Ser Ile Ser Val Ser Asn Cys Gln Ile Gln Glu Asn Val Asp
                565                 570                 575

Ile Ser Thr Val Tyr Gln Ile Phe Pro Asp Glu Val Leu Gly Ser Gly
            580                 585                 590

Gln Phe Gly Ile Val Tyr Gly Gly Lys His Arg Lys Thr Gly Arg Asp
        595                 600                 605

Val Ala Ile Lys Ile Ile Asp Lys Leu Arg Phe Pro Thr Lys Gln Glu
    610                 615                 620

Ser Gln Leu Arg Asn Glu Val Ala Ile Leu Gln Asn Leu His His Pro
625                 630                 635                 640

-continued

Gly Val Val Asn Leu Glu Cys Met Phe Glu Thr Pro Glu Arg Val Phe
              645                 650                 655

Val Val Met Glu Lys Leu His Gly Asp Met Leu Glu Met Ile Leu Ser
          660                 665                 670

Ser Glu Lys Gly Arg Leu Pro Glu His Ile Thr Lys Phe Leu Ile Thr
          675                 680                 685

Gln Ile Leu Val Ala Leu Arg His Leu His Phe Lys Asn Ile Val His
      690                 695                 700

Cys Asp Leu Lys Pro Glu Asn Val Leu Leu Ala Ser Ala Asp Pro Phe
705                 710                 715                 720

Pro Gln Val Lys Leu Cys Asp Phe Gly Phe Ala Arg Ile Ile Gly Glu
              725                 730                 735

Lys Ser Phe Arg Arg Ser Val Val Gly Thr Pro Ala Tyr Leu Ala Pro
          740                 745                 750

Glu Val Leu Arg Asn Lys Gly Tyr Asn Arg Ser Leu Asp Met Trp Ser
          755                 760                 765

Val Gly Val Ile Ile Tyr Val Ser Leu Ser Gly Thr Phe Pro Phe Asn
      770                 775                 780

Glu Asp Glu Asp Ile His Asp Gln Ile Gln Asn Ala Ala Phe Met Tyr
785                 790                 795                 800

Pro Pro Asn Pro Trp Lys Glu Ile Ser His Glu Ala Ile Asp Leu Ile
              805                 810                 815

Asn Asn Leu Leu Gln Val Lys Met Arg Lys Arg Tyr Ser Val Asp Lys
          820                 825                 830

Thr Leu Ser His Pro Trp Leu Gln Asp Tyr Gln Thr Trp Leu Asp Leu
          835                 840                 845

Arg Glu Leu Glu Cys Lys Ile Gly Glu Arg Tyr Ile Thr His Glu Ser
      850                 855                 860

Asp Asp Leu Arg Trp Glu Lys Tyr Ala Gly Glu Gln Gly Leu Gln Tyr
865                 870                 875                 880

Pro Thr His Leu Ile Asn Pro Ser Ala Ser His Ser Asp Thr Pro Glu
              885                 890                 895

Thr Glu Glu Thr Glu Met Lys Ala Leu Gly Glu Arg Val Ser Ile Leu
          900                 905                 910

<210> SEQ ID NO 2
<211> LENGTH: 23
<212> TYPE: RNA
<213> ORGANISM: Artificial Sequence
<220> FEATURE:
<223> OTHER INFORMATION: synthesized

<400> SEQUENCE: 2
uggcaguguc uuuagcuggu ugu                                     23

<210> SEQ ID NO 3
<211> LENGTH: 22
<212> TYPE: RNA
<213> ORGANISM: Artificial Sequence
<220> FEATURE:
<223> OTHER INFORMATION: synthesized

<400> SEQUENCE: 3
cauuugccuu gcagaacugc ca                                      22

```
<210> SEQ ID NO 4
<211> LENGTH: 22
<212> TYPE: RNA
<213> ORGANISM: Artificial Sequence
<220> FEATURE:
<223> OTHER INFORMATION: synthesized

<400> SEQUENCE: 4
cauuugccuu gcagagagaa aa                                          22
```

THERAPEUTIC COMPOSITIONS FOR BREAST CANCER CONTAINING PROTEIN KINASE D1 INHIBITOR

TECHNICAL FIELD

The present invention relates to a composition for inhibiting breast cancer stem cells containing a protein kinase D1 inhibitor and an anticancer adjuvant for preventing recurrence of breast cancer.

BACKGROUND ART

Breast cancer is the most common tumor and ranks top in causes of woman tumor-related deaths worldwide [1]. Despite efforts to improve the survival rate of patients, there are still problems related with breast cancer treatment including metastasis and drug resistance [2, 3]. Tumors consist of cancer stem cells (CSCs) and non-tumorigenic cells that form tumor mass [4]. The CSCs are considered as a cause of tumor, tumor metastasis, drug resistance, and tumor recurrence [5]. In particular, breast cancer stem cells (BCSCs) has a characteristic of stem cells and are characterized by expression of cell surface markers CD44+/CD24− [6]. Different miRNAs are involved in the formation and regulation of human breast cancer stem cells [7], and according to preceding studies, ectopic expression of miR-34c inhibits migration of epithelial-mesenchymal cells and reduces self-renewal capacity in human breast cancer stem cells [8].

Serine/threonine-protein kinase D1 (PKD1) acts as diacylglycerol and protein kinase C (PKC) effectors to mediate stimulatory activity [9]. PKD/PKCμ related cellular processes were activated by two phosphorylations through PKC-dependent phosphorylation (Ser744/Ser748) and PKC-independent autophosphorylation (Ser910) [10-13]. Therefore, PRKD1 is considered as a major regulator in many cellular processes including a NF-kB signaling pathway, cell cycle progression, DNA synthesis, and regulation of other pathogenic conditions [14-16].

In breast cancer, microRNAs regulate apoptosis, tumor formation and angiogenesis. A major regulator of tumor suppression, miR-34, is a direct transcriptional target for a tumor inhibitor p53, and a miR-34a promoter region includes a p53-binding site [17]. In breast cancer studies, the miR-34a plays a role in inhibiting cell survival by up-regulating p53 after irradiation after DNA damage [18]. In addition, the miR-34a promoted tumor apoptosis by targeting Bcl-2 and SIRT1 [19]. Therefore, the miR-34a is associated with a target that induces breast cancer.

PRIOR ART DOCUMENT

Non-Patent Document

Cui J et al., Oncogene 2015; 34:3895-3907
Chaffer C L, Weinberg R A. Science 2011; 331:1559-1564.
Li L et al., Clinical and experimental medicine. 2013; 13:109-117.
Visvader J E, Lindeman G J. Nat. Rev. Cancer 2008; 8:755-768.
Park E Y et al., Cancer research 2014; 74:7573-7582.
Liu S, Clouthier S G, Wicha M S. Journal of mammary gland biology and neoplasia 2012; 17:15-21.
Schwarzenbacher D, Balic M, Pichler M. International journal of molecular sciences 2013; 14:14712-14723.
Yu F et al., The Journal of biological chemistry 2012; 287:465-473.
Fu Y, Rubin C S. EMBO reports 2011; 12:785-796.
Iglesias T, Waldron R T, Rozengurt E. The Journal of biological chemistry 1998; 273:27662-27667.
Valverde A M et al., Proceedings of the National Academy of Sciences of the United States of America. 1994; 91:8572-8576.
Rozengurt E, Rey O, Waldron R T. The Journal of biological chemistry 2005; 280:13205-13208.
Jacamo R et al., The Journal of biological chemistry 2008; 283:12877-12887.
Storz P, Toker A. The EMBO journal 2003; 22:109-120.
Sinnett-Smith J et al., The Journal of biological chemistry 2004; 279:16883-16893.
Harikumar K B et al., Molecular cancer therapeutics 2010; 9:1136-1146.
Misso G et al., Molecular therapy Nucleic acids 2014; 3:e194.
Achari C et al., BMC cancer 2014; 14:538.
Kato M et al., Oncogene 2009; 28:2419-2424.
Du C et al., Cancer research 2009; 69:1117-1124.
Jope R S, Yuskaitis C J, Beurel E. Neurochemical research 2007; 32:577-595.
Yuan J et al., Frontiers in physiology 2012; 3:60.
Jaggi M et al., Frontiers in bioscience: a journal and virtual library 2007; 12:3757-3767.
Sundram V, Chauhan S C, Jaggi M. Molecular Cancer Research 2011; 9:985-996.
Eiseler T et al., Breast cancer research: BCR 2009; 11:R13.
Bowden E T, Barth M, Thomas D, Glazer R I, Mueller S C. Oncogene 1999; 18:4440-4449.
Borges S et al., Breast cancer research: BCR 2013; 15:R66.
Liu C et al., Nature medicine 2011; 17:211-215.
Nails D et al., PloS one 2011; 6:e24099.
Stankevicins L et al., Radiation oncology 2013; 8:231.
Guessous F et al., Cell cycle 2010; 9:1031-1036.
Jaggi M et al., Cancer research 2005; 65:483-492.
Ciani L, Salinas P C. Nat Rev Neurosci. 2005; 6:351-362.
Kroon J et al., Oncotarget 2014; 5:8986-8994. doi:10.18632/oncotarget.1510

DISCLOSURE

Technical Problem

An object of the present invention is to provide pharmaceutical compositions for inhibiting breast cancer proliferation and metastasis more effectively.

Another object of the present invention is to provide an adjuvant for restoring drug sensitivity of anticancer agent-resistant breast cancer more effectively.

Yet another object of the present invention is to provide pharmaceutical compositions for inhibiting recurrence of breast cancer more effectively.

Technical Solution

The present inventors found that PRKD1 overexpressed in MCF-7-ADR cells was inhibited by miR-34a. In addition, the PRKD1 activated self-renewal capacity in breast cancer stem cells through glycogen synthase kinase 3 (GSK3)/β-catenin signaling and contributed to the removal of drug resistance. These results indicate that the PRKD1 as a new target of miR-34a can play an important role in the treatment of human breast cancer.

The present invention relates to a pharmaceutical composition for inhibiting the growth of cancer stem cells containing a protein kinase D1 expression or activity inhibitor as an active ingredient.

Further, the protein kinase D1 of the present invention may have an amino acid sequence of SEQ ID NO: 1, and the protein kinase D1 is not limited to the amino acid sequence of SEQ ID NO: 1 and includes an analogue thereof.

Further, the protein kinase D1 expression inhibitor of the present invention may be any one selected from the group consisting of an antisense nucleotide complementarily binding to mRNA of a protein kinase D1 gene, a short interfering RNA, a short hairpin RNA, and miR34a.

Further, the protein kinase D1 activity inhibitor of the present invention may be any one selected from the group consisting of compounds that specifically bind to the protein kinase D1, peptides, peptide mimetics, aptamers, antibodies and CRT0066101.

Further, the cancer of the present invention may be selected by cancer stem cell markers CD44+ and CD24−.

Further, the cancer of the present invention is preferably one selected from the group consisting of breast cancer, liver cancer, intestine cancer, cervical cancer, kidney cancer, stomach cancer, prostate cancer, brain tumor, lung cancer, uterine cancer, colon cancer, bladder cancer, blood cancer and pancreatic cancer and more preferably breast cancer, but it is not limited thereto.

Further, in order to avoid recurrence and metastasis of cancer cells and completely remove cancer, beyond the limitations of current cancer therapies that only attack cancer cells, it is necessary to remove cancer stem cells by targeting the cancer stem cells having stem cell characteristics. The present invention may inhibit the growth of cancer stem cells, particularly breast cancer stem cells and inhibit the cancer stem cells to prevent cancer recurrence.

The present invention relates to a pharmaceutical composition for inhibiting proliferation and metastasis of breast cancer containing a protein kinase D1 expression or activity inhibitor as an active ingredient.

Further, the protein kinase D1 inhibitor may inhibit stemness of breast cancer cells.

The present invention relates to an anti-cancer adjuvant for preventing recurrence of breast cancer containing a protein kinase D1 expression or activity inhibitor as an active ingredient.

Further, since the composition of the present invention significantly inhibits the growth of breast cancer stem cells, the present invention relates to an anti-cancer adjuvant capable of inhibiting recurrence of breast cancer.

The present invention provides a method for inhibiting breast cancer stem cells including a step of treating a protein kinase D1 expression or activity inhibitor to a subject.

Further, the present invention provides a method for measuring prognosis of breast cancer including a step of determining recurrence of breast cancer by verifying whether the protein kinase D1 is expressed or activated in a subject.

The protein kinase D1 is expressed in the breast cancer stem cells, and when the protein kinase D1 is inhibited, the growth of the breast cancer stem cells is significantly inhibited, and thus, the protein kinase D1 expression or activity inhibitor may be usefully used for inhibition of the breast cancer stem cells. Further, since there is a risk of recurrence of breast cancer due to the breast cancer stem cells, prognosis of breast cancer may be measured by measuring whether the protein kinase D1 is expressed or activated.

The composition of the present invention may be used alone or in combination with radiation therapy, chemotherapy, and a method using a biological response modifier.

The composition of the present invention contains 0.0001 to 50 wt % with respect to the total weight of the therapeutic composition.

The composition of the present invention may further contain one or more active ingredients that exhibit the same or similar functions. The composition of the present invention may be administered orally or parenterally during clinical administration and used in the form of a general pharmaceutical preparation.

The composition of the present invention may be administered in a form of a composition that further includes a pharmaceutically acceptable carrier. The pharmaceutically acceptable carrier includes, for example, one or more of water, saline, phosphate buffered saline, dextrin, glycerol, ethanol, and combinations thereof. The composition may be formulated to provide a rapid release, or a sustained or delayed release of the active ingredient after administration.

When the inhibitor for the protein of the present invention is an antibody, the pharmaceutically acceptable carrier may consist of a minimum amount of auxiliary material such as a wetting agent, an emulsifying agent, a preservative or a buffer, which increase the storage life or effectiveness of a binding protein.

The composition of the present invention may include a pharmaceutically acceptable and physiologically acceptable adjuvant, and the adjuvant may include excipients, disintegrants, sweeteners, binders, coating agents, swelling agents, lubricants, glydents or solubilizers.

In addition, the composition of the present invention may be formulated into a pharmaceutical composition containing at least one pharmaceutically acceptable carrier in addition to the above-described active ingredients for administration.

The pharmaceutical carrier which is accepted in the composition formulated into a liquid solution is suitable for sterilization and living bodies and may use a saline solution, sterile water, a ringer's solution, buffered saline, an albumin injection solution, a dextrose solution, a maltodextrin solution, glycerol, ethanol and combinations of one or more components thereof, and if necessary, other general additives such as antioxidants, buffers, and bacteriostats may be added. Further, the pharmaceutical carrier may be formulated by injectable formulations such as aqueous solutions, suspensions, and emulsions, pills, capsules, granules or tablets by additionally adding diluents, dispersants, surfactants, binders and lubricants. Furthermore, the pharmaceutical carrier may be preferably formulated according to each disease or ingredient by using, as a proper method of the corresponding field, a method disclosed in Remington's Pharmaceutical Science, Mack Publishing Company, Easton Pa.

The pharmaceutical formulations of the composition of the present invention may include granules, powders, coated tablets, tablets, capsules, suppositories, syrups, juices, suspensions, emulsions, drops or injectable solutions, and sustained release formulations of active compounds.

The composition of the present invention may be administered by a general method through intravenous, intraarterial, intraperitoneal, intramuscular, intraarterial, intraperitoneal, intrasternal, transdermal, intranasal, inhalation, topical, rectal, intraocular, or intradermal routes.

An "effective dose" means an amount required to achieve an effect of inhibiting the proliferation and metastasis of breast cancer and the growth of stem cells. Accordingly, the "effective dose" of the active ingredient of the present invention may be adjusted according to various factors including a type of disease, severity of the disease, types and contents of an active ingredient and other ingredients contained in the composition, a type of formulation, and an age, a weight, a general health status, a gender, and a diet of a patient, an administration time, an administration route, a secretion ratio of the composition, a treating period, and simultaneously used drugs. In the case of an adult, when the inhibitor of the gene or protein is administered one to several times a day, 0.01 ng/kg to 10 mg/kg in the case of siRNA, 0.1 ng/kg to 10 mg/kg in the case of the antisense oligonucleotide for mRNA of the gene, 0.1 ng/kg to 10 mg/kg in the case of the compound, and 0.1 ng/kg to 10 mg/kg of the monoclonal antibody for the protein may be administered.

Furthermore, it is apparent to those skilled in the art that the PRKD1-targeting siRNA, an antibody thereof, and the like are prepared as follows.

Antisense Nucleotide

An antisense nucleotide binds (hybridizes) to a complementary base sequence of DNA, immature-mRNA, or mature mRNA as defined in a Watson-click base pair, to interfere with the flow of genetic information as a protein in DNA. The nature of the antisense nucleotide which is specific to a target sequence becomes exceptionally multi-functional. Since the antisense nucleotides are long chains of monomer units, the antisense nucleotides may be easily synthesized with respect to the target RNA sequence. Many recent studies have verified the utility of the antisense nucleotides as a biochemical means for studying the target protein (Rothenberg et al., J. Natl. Cancer Inst., 81:1539-1544, 1999). Since there has been much progress in fields of oligonucleotide chemistry and nucleotide synthesis having improved cell line adsorption, target binding affinity and nuclease resistance, the use of the antisense nucleotide may be considered as a novel type of inhibitor.

Peptide Mimetics

The peptide mimetics is a peptide or non-peptide that inhibits a binding domain of the PRKD1 protein leading to PRKD1 activity. Major residues of a nonhydrolyzable peptide analog may be produced by using β-turn dipeptide cores (Nagai et al. Tetrahedron Lett 26:647, 1985), keto-methylene pseudopeptides (Ewenson et al. J Med chem 29:295, 1986; and Ewenson et al. in Peptides: Structure and Function (Proceedings of the 9th American Peptide Symposium) Pierce chemical co. Rockland, Ill., 1985), azepine (Huffman et al. in Peptides: chemistry and Biology, G. R. Marshall ed., EScOM Publisher: Leiden, Netherlands, 1988), benzodiazepine (Freidinger et al. in Peptides; chemistry and Biology, G. R. Marshall ed., EScOM Publisher: Leiden, Netherlands, 1988), β-aminoalcohol (Gordon et al. Biochem Biophys Res commun 126:419 1985), and a substituted gamma-lactam ring (Garvey et al. in Peptides: chemistry and Biology, G. R. Marshall ed., EScOM Publisher: Leiden, Netherlands, 1988).

siRNA Molecule

It is preferred that a sense RNA and an antisense RNA form a double stranded RNA molecule, in which the sense RNA is a siRNA molecule including the same nucleic acid sequence as the target sequence of some consecutive nucleotides of the PRKD1 mRNA. The siRNA molecule is preferably composed of a sense sequence consisting of 10 to 30 bases selected in the nucleotide sequence of the PRKD1 gene and an antisense sequence complementarily binding to the sense sequence, but it is not limited thereto. Any double-stranded RNA molecule having a sense sequence capable of complementarily binding to the base sequence of the PRKD1 gene may be used. Most preferably, the antisense sequence has a sequence complementary to the sense sequence.

Antibody

The PRKD1 antibody may be prepared through PRKD1 injection or commercially available. Further, the antibody includes a polyclonal antibody, a monoclonal antibody, and a fragment capable of binding to an epitope.

The polyclonal antibodies can be produced by a conventional method of obtaining serum containing the antibodies by injecting the PRKD1 into an animal and collecting blood from the corresponding animal. Such polyclonal antibodies may be purified by any method known in the art and made from any animal species host, such as goats, rabbits, sheep, monkeys, horses, pigs, cows, dogs and the like.

The monoclonal antibodies may be prepared using any technology that provides the production of antibody molecules through the cultivation of continuous cell lines. Such a technology is not limited thereto, but includes a hybridoma technology, a human B-cell line hybridoma technology, and an EBV-hybridoma technology (Kohler G et al., Nature 256:495-497, 1975; Kozbor D et al., J Immunol Methods 81:31-42, 1985; cote R J et al., Proc Natl ACad Sci 80:2026-2030, 1983; and cole S P et al., Mol cell Biol 62:109-120, 1984).

Further, antibody fragments containing specific binding sites for the PRKD1 may be prepared. For example, although not limited thereto, $F(ab')_2$ fragments may be prepared by decomposing an antibody molecule into pepsin, and Fab fragments may be prepared by reducing disulfide bridges of the $F(ab')_2$ fragments. Alternatively, monoclonal Fab fragments having the desired specificity may be identified quickly and easily by decreasing a Fab expression library (Huse W D et al., Science 254: 1275-1281, 1989).

The antibody may bind to a solid substrate to facilitate subsequent steps such as washing or separation of the complex. The solid substrate includes, for example, a synthetic resin, nitrocellulose, a glass substrate, a metal substrate, glass fibers, microspheres, microbeads, and the like. In addition, the synthetic resin includes polyester, polyvinyl chloride, polystyrene, polypropylene, PVDF, nylon, and the like.

Aptamer

The aptamer is a single-stranded nucleic acid (DNA, RNA or modified nucleic acid) that has its own stable tertiary structure and is capable of binding to a target molecule with high affinity and specificity. After an aptamer discovery technology called SELEX (Systematic Evolution of Ligands by EXponential enrichment) is first developed Ellington, A D and Szostak, J W., Nature 346:818-822, 1990), many aptamers that can bind to various target molecules, including small molecules, peptides, and membrane proteins have been continuously discovered. The aptamer is comparable to the monoclonal antibody due to its characteristic capable of binding to a target molecule with unique high affinity (usually a pM level) and specificity, and there is a high possibility to be an alternative antibody, especially as a "chemical antibody".

Various advantages and features of the present disclosure and methods accomplishing thereof will become apparent from the following description of exemplary embodiments with reference to the accompanying drawings. However, the present disclosure is not limited to the following exemplary embodiments but may be implemented in various different forms. The exemplary embodiments are provided only to complete disclosure of the present disclosure and to fully provide a person having ordinary skill in the art to which the present disclosure pertains with the category of the disclosure, and the present disclosure will be defined by the appended claims.

Advantageous Effects

According to the present invention, stemness of breast cancer cells is inhibited by inhibiting expression and/or activity of PRKD1. Therefore, an inhibitor for the expression or activity of PRKD1 can be used for inhibiting proliferation, metastasis or recurrence by stemness of breast cancer and restore the drug sensitivity of breast cancer.

DESCRIPTION OF DRAWINGS

FIGS. 1A to 1C illustrate that PRKD1 is a new target of miR-34a. FIG. 1A: PRKD1 mRNA expression and miR-34a expression were quantified by qRT-PCR in various human breast cancer cell lines. FIG. 1B: Protein, mRNA and total RNA obtained after transfection of a miRNA-34 variant and 48 hours. Western blot is a representative value of three independent experiments. β-actin was used as a loading control and qRT-PCR was performed to verify expression of the PRKD1 mRNA and the miR-34 variant. Expression levels of miR-34a, b, and c were detected after ectopic expression of miR-34a, b and c, respectively. FIG. 1C: miR-34a binding site and reporter construct predicted from wild type/mutant PRKD1 3'-UTR. The activity of the 3'-UTR reporter construct was normalized as compared with the activity of a cotransfected phRL-Luc vector. A graph is illustrated as mean± standard deviation obtained from three independent experiments. *$p<0.05$; $p<0.001$; *$p<0.0001$.

FIGS. 2A and 2B: A miR-34a precursor and PRKD1 siRNAs (15 nM) were transfected into MCF-7-ADR cells and expression of miR-34a and PRKD1 was verified by qRT-PCR. Western blot analysis of GSK3/β-catenin signaling was performed. β-actin was used as a loading control. FIG. 2C: It is illustrated that basic phosphorylation and expression of PKD/PKCμ in MCF-7-ADR cell-derived tumor cells as compared with 2-dimensional culture MCF-7 cells. FIG. 2D: At a magnification of 400×, a confocal representative image of formation of tumorspheres was captured using the Olympus IX71. A size bar is 50 μm. FIG. 2E: Cell surface expression of breast cancer stem cell markers in MCF-7-ADR cultured cells is analyzed. A histogram shows results of fiver independent experiments. A percentage represents the number of cells in each quartile. A bar represents each sample performed three times, and an error bar represents ±standard deviation. *$p<0.05$; $p<0.001$; *$p<0.0001$.

FIG. 3A: Western blot analysis of GSK3/β-catenin signaling after treatment with 0.1 to 10 μM of CRT0066101. The blot represents five independent experiments. β-actin was used as a loading control. FIG. 3B: Tumorspheres were treated with distilled water (control) or d1 μM or 5 μM CRT0066101. A representative confocal image of formation of tumorspheres was photographed at 400× magnification using the Olympus IX71. A size bar is 50 μm. A graph showed the number of tumorspheres per 2000 cells. FIG. 3C: CD44+/CD24-expression on the surface of MCF-7-ADR cells after treatment with CRT0066101 is analyzed. A histogram illustrates a result of three independent experiments. A percentage represents the number of cells in each quartile. *$p<0.001$; $p<0.0001$; *$p<0.0001$.

FIG. 4A: Cell survival rate was detected after MCF-7-ADR cells were transfected with a control vector or PRKD1 siRNA. After PRKD1 expression was knocked down, doxorubicin was administered at different doses and cell survival rate was measured. FIG. 4B: Caspase-3 activity level after down-regulation of PRKD1 and caspase-3 activity level after doxorubicin treatment. FIG. 4C: Result of WST-8 analysis after 70-hour treatment (0.1 to 5 μM) of CRT0066101 in MCF-7-ADR cells. An optical density was measured at 450 nm. FIG. 4D: The caspase-3 activity was measured after treatment of 1 μM/2 μM CRT0066101 or 10 μM doxorubicin. Relative caspase-3 activity was measured at 405 nm. FIG. 4E: A photograph of Annexin V/PI-stained cells was taken with a confocal microscope at 200× magnification. Size bar: 50 μm. Data were represented as mean± standard deviation. *$p<0.05$; **$p<0.001$.

FIG. 5A: In a control and a miR-34a overexpressed tumor, expression of PRKD1 mRNA was measured by qRTPCR. FIG. 5B: In a control and a miR-34a overexpressed tumor, in order to detect expression of PKCμ and PCNA, immunohistochemistry was performed. Magnification: 200×; Size bar: 10 μm. FIG. 5C: TUNEL analysis and DAPI straining were performed. Magnification: 400×; Size bar: 20 μm. FIG. 5D: CRT0066101 (65 mg/kg) was orally administered to tumor established in a nude mouse daily for 4 weeks. A xenograft result of three representative mice is illustrated. FIG. 5E: As compared with control tumor, a volume of tumor treated with CRT0066101 was reduced. However, a change in mouse's weight was not detected. FIG. 5F: Western blot analysis of phosphorylated PRKD1 and GSK3/β-catenin signaling was performed. β-actin was used as a loading control. FIG. 5G: An immunofluorescence photograph showing TUNEL and Ki67 in a control and CRT0066101 treated tumor. Data were represented as mean± standard deviation. *$p<0.05$, **$p<0.001$.

FIGS. 7A and 7B verify expression levels of miR-34b and miR-34c in various breast cancer cell lines, respectively, by qRT-PCR.

FIG. 9A: After transfection with miR-34a inhibitor in MCF-7 cells, the expression level of miR-34a was verified by qRT-PCR. FIG. 9B: GSK3/β-catenin signaling was measured by western blot analysis. β-actin was used as a loading control.

FIGS. 10A and 10B: Expression levels of OCT4 and SOX2 were verified by qRT-PCR.

FIG. 11A: The miR-34a was highly expressed in spherical MCF-7 cells, FIG. 11B: The PRKD1 was highly expressed in MCF-7-ADR breast cancer stem cells.

FIG. 12A: As the western blot analysis result, an effect of CRT0066101 is shown in MCF-7 cells. FIG. 12B: A result of WST-8 analysis after treatment (0.1 to 5 μM) of CRT0066101 in MCF-7 cells is illustrated.

FIG. 13A: There is no correlation between expression of miR-34a and expression of PRKD1 in various cell lines. FIG. 13B: Overall survival rate according to a PRKD1 expression level in a TCGA clinic data set is illustrated.

MODES OF THE INVENTION

Figure 1A:
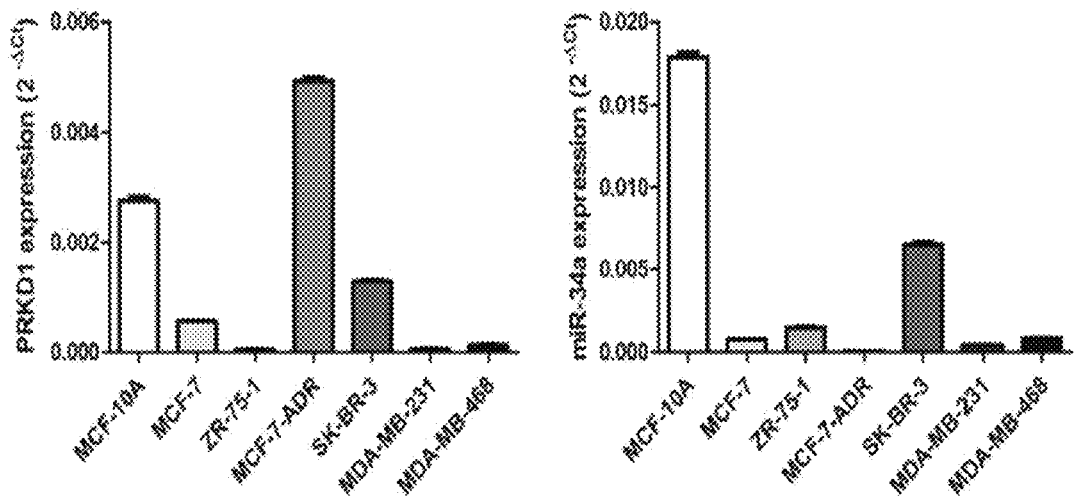

Hereinafter, configurations of the present invention will be described in more detail with reference to detailed Examples. However, it is apparent to those skilled in the art that the scope of the present invention is not limited to only the disclosure of Examples.

Chemical Drug and Reagent

CRT0066101 was purchased from R&D Systems (Minneapolis, Minn., USA); this drug was resuspended in sterile distilled water and used for in vivo studies. To treat CRT0066101, MCF-7-ADR cells (American Type Culture Collection, Manassas, Va., USA) were seeded and 0.1 to 10 μM CRT0066101 was added and incubated for 1 hour. WST-8 was purchased from Enzo Life Sciences, Inc. (Farmingdale, N.Y., USA). PRKD1 siRNA and scrambled siRNA (Santa Cruz Biotechnology, Santa Cruz, Calif., USA) were transfected by using Lipofectamine RNAiMAX (Invitrogen, Carlsbad, Calif., USA).

Cell Culture and Transfection

The breast adenocarcinoma MCF7, MCF-7-ADR and MDAMB-231 cell lines (American Type Culture Collection) were incubated in DMEM (Dulbecco's modified Eagle's Medium; Welgene, Daejeon, South Korea) and 10% FBS (Welgene), 1% penicillin, streptomycin were supplemented in a wet incubator at 37° C. under 5% $CO_2$. For RNAi transfection, MCF-7-ADR cells were seeded in a medium without antibiotics in a 10-cm plate. After 24 hours, cells were transfected with PRKD1 siRNA using Lipofectamine RNAiMAX (Invitrogen). After 48 hours, the cells were collected and analyzed by western blot or resuspended in a breast cancer mammosphere medium. For microRNA transfection, MCF-7-ADR cells were incubated with a miRNA precursor (miR-34a/b/c) for 48 hours using a siPORT NeoFX transfection agent (Ambion; Thermo Fisher, St. Louis, Mo., USA). A miRNA precursor and a negative control precursor were purchased from Thermo Fisher.

qRT-PCR

Quantitative reverse-transcription PCR (qRT-PCR) was performed according to manufacturer's instructions in a SYBR Green-based method using an RG 3000 apparatus (Corbett Robotics, San Francisco, Calif., USA). An ABI-7500 apparatus (Thermo Fisher) was used to evaluate PRKD1 expression in various breast cancer cell lines. All oligonucleotide primers were designed with DNASTAR (Madison, Wis., USA). All qRT-PCR graphs were obtained by using relative $C_t$ ($\Delta\Delta C_t$) values.

Western Blotting and Antibodies

A total of 30 μg of a protein extract was isolated by 8% SDS-PAGE and the protein was electrophoretically transferred to a PVDF membrane. The primary antibodies used were phosphorylated PKD/PKCμ (Ser916), GSK3β, phosphorylated GSK3α (Ser21)/β (Ser9), and β-catenin. These antibodies were purchased from Cell Signaling Technology (Danvers, Mass., USA) and the PKD/PKCμ antibody was purchased from Santa Cruz Biotechnology. (β-actin (Bethyl Laboratories, Montgomery, Tex., USA) was used as a loading control. The membrane was washed with 1×PBS/0.1% Tween 20 and the bound proteins were detected with an enhanced chemiluminescent reagent (Amersham Pharmacia Biotech, Parsippany, N.J., USA).

Luciferase Analysis Method

The 3'-UTR reporter construct of PRKD1 was cloned into a pGL3-control vector and the 3'-UTRs of PRKD1 were amplified from the genomic DNA of HEK293T cells. The miR-34 seed sequence from PRKD1 w was mutated by a PCR-based method and the reporter construct was verified by sequencing. HEK293T cells were transiently transfected with a 3'-UTR reporter construct (1.5 μg per well in a 6-well plate) and 15 nM of a miR-34 family precursor (Ambion) by using Lipofectamine 2000 (Invitrogen). The activity of the 3'-UTR reporter construct was normalized to the activity of cotransfected pCMV-hRL (40 ng per well in a 6-well plate, Promega). After incubation for 24 hours, the cells were lysed with a 1× passive lysis buffer, and the activity was measured using a Dual Luciferase Assay kit (Promega) according to the manufacturer's instructions.

Tumorsphere Formation Assay (TSA)

For incubation of tumorspheres, cells (2000 cells/mL) were suspended and incubated in serum-free DMEM/F12 (welGENE) containing 1% penicillin, B27 (1:50; Gibco; Thermo Fisher), 20 ng/mL of an epidermal growth factor (Prospec, East Brunswick, N.J., (WelGENE) 5 mg/mL of insulin (Sigma-Aldrich, St. Louis, Mo., USA) and 0.4% bovine serum albumin (Sigma-Aldrich). After about 10 days, the plate was analyzed and formation of tumorspheres was verified and quantified with a microscope (Olympus IX71; Olympus, Tokyo, Japan). In order to count the number of tumorspheres, MCF-7-ADR cells were filtered and quantified by a strainer (BD Biosciences, East Rutherford, N.J., USA) having a pore size of 70 μm. Treatment with CRT0066101 was performed on 6-th day and 8-th day after incubation.

Surface Marker Analysis Using Flow Cytometry

Cells were collected after transfection with RNAi of PRKD1 or CRT0066101 treatment and expression of CD44+/CD24-surfaces was evaluated. The cells were washed with 2% FBS, stained with anti-CD44 (APC-conjugated; BD Biosciences) and anti-CD24 (BD Biosciences) in a PBS containing 2% FBS, and placed on ice in the dark for 30 minutes. The cells were washed again with a cold PBS buffer, loaded with >10,000 cells in a BD CantoII flow cytometer (BD Biosciences), and then analyzed by flow cytometry using FACSDiVa software (BD Biosciences).

Analysis of Cell Survival Rate

MCF-7-ADR cells were placed in a 24-well plate and incubated for 72 hours together with CRT0066101 at various concentrations (0.1, 0.5, 1, 5, and 10 μM). Cell survival rate was analyzed by WST-8 assay (Sigma-Aldrich) and an optical density was measured at 450 nm using a microplate reader.

Fluorescence Immunohistochemistry

A control or miR-32a overexpressed tumor and a carrier or CRT0066101 treated tumor were cut and paraffin-treated slides were used. The paraffin was removed from the slides, rehydrated 3 to 4 times in Histoclear, and then passed sequentially through ethanol at different concentrations (100%, 95%, 80%, and 70%). Antigen reconstitution was performed by immersing fragments in a 0.01M citric acid solution (pH 6.0) and boiling the fragments in a microwave for 15 minutes. In the case of TUNEL analysis, an in-situ apoptosis detection kit, a fluorescent material (Roche, Indianapolis, USA) labeled apoptotic cells, and a Ki-67 primary antibody (Vector Lab, USA) were applied to the fragments and incubated at 4° C. overnight. Thereafter, the slides were incubated with DAPI and secondary antibody for two hours. Finally, the slides were treated with a mounting solution (Dako) and a photograph was taken with a confocal microscope (Zeiss).

Preparation of Breast Cancer Xenografted Mice

All studies, including the use of nude mice, were approved by the committee on animal protection and use of the Yonsei University Medical center (2015-0087) and performed under conditions according to facilities without specific pathogens and the guideline of the committee. Mice were anesthetized with 150 µl saline/zoletil/rompun (7:1:1) outside each femoral region and subcutaneously injected with $1.5 \times 10^6$ of MCF-7-ADR cells. Six mice were randomly grouped and started to be treated from 10-th day after tumor graft. CRT0066101 was administered orally to a tumor-bearing animal and administered with 1.6 mg/kg every time, 5 times per week, for 4 weeks. The tumor size was measured every 3 to 4 days using a caliper from formation of touched tumor to termination and the tumor volume was calculated by Equation of length×width$^2$×0.5236. The mice were sacrificed in a 7.5% $CO_2$ chamber and tumors were isolated and used for immunohistochemistry and other assays.

Result 1: MiR-34a Inhibits PRKD1 in MCF-7-ADR Cells

Figure 1B:
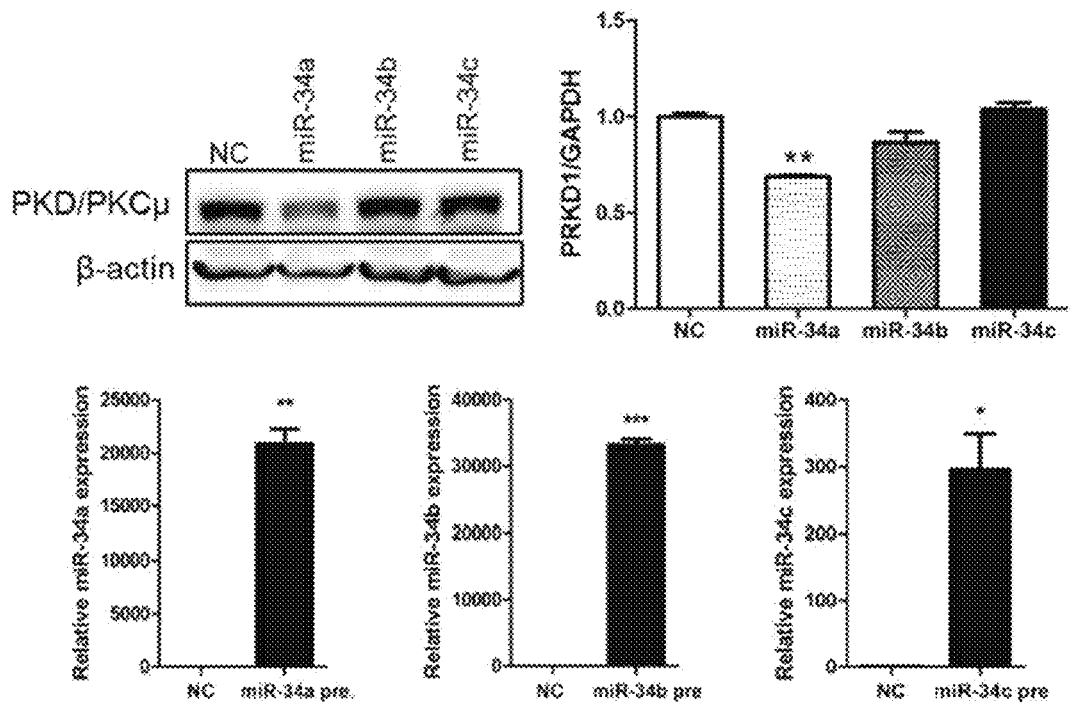
Figure 1C:
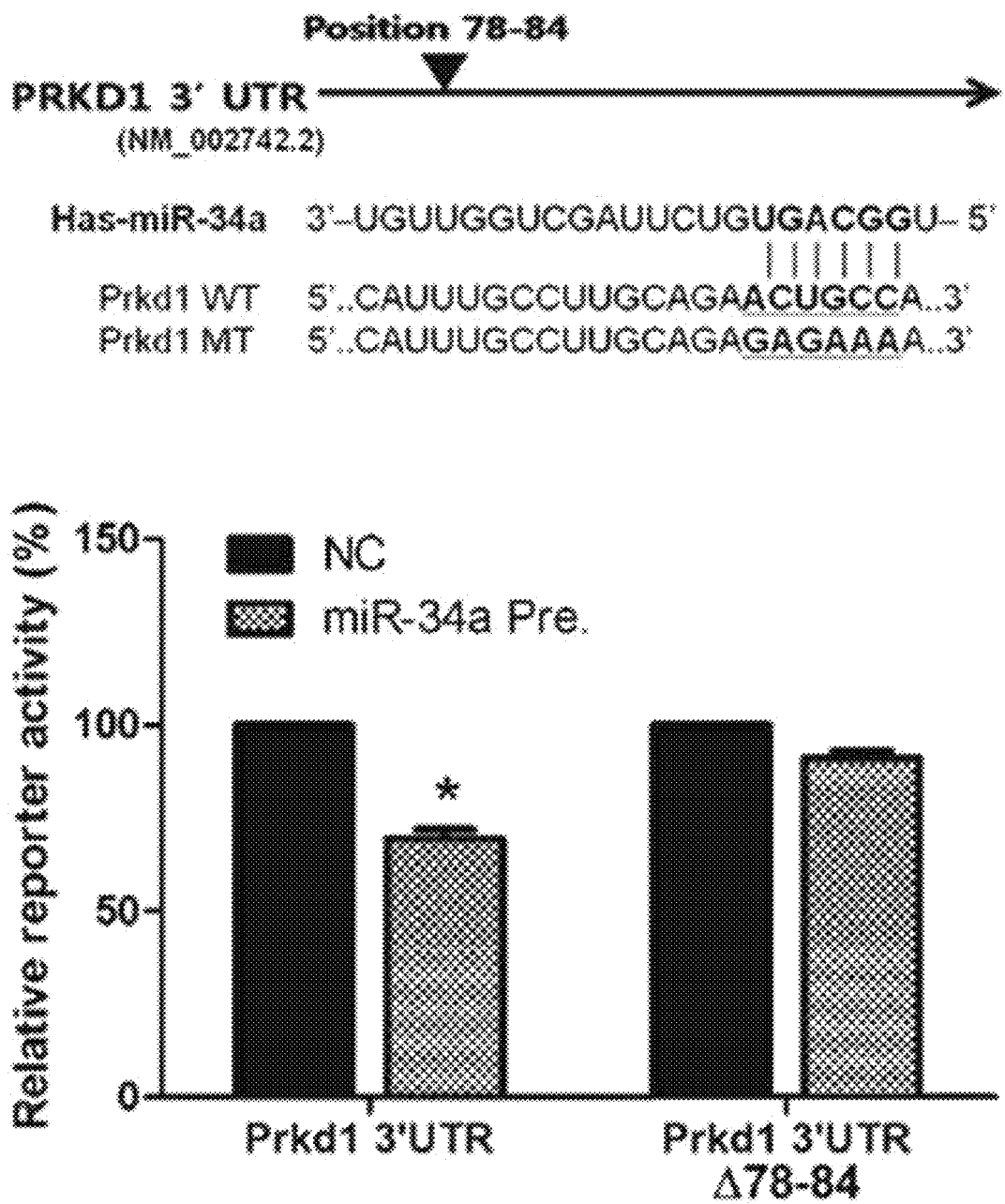

PRKD1 expression was evaluated in breast cancer cell lines including MCF-10A, MCF-7, ZR-75-1, MCF-7-ADR, SK-BR-3, MDA-MB-231 and MDAMB-468. As a result, the PRKD1 expression level was increased in MCF-7-ADR cells (see FIG. 1A). The present inventors determined miRNA capable of regulating PRKD1 by using a microRNA predictive on-line database [miRanda (http://www.microrna.org/microrna/home.do) and TargetScan (http://www.targetscan.org/)]. Considering that miR-34 is a candidate regulator, PRKD1 mRNA expression and protein translation levels were measured after ectopic expression of miR-34a, miR-34b and miR-34c. Although miR-34a, miR-34b and miR-34c have the same seed sequence, the result showed that PKD/PKCµ was down-regulated only by miR-34a (FIG. 1B). In order to verify whether miR-34a binds to PRKD1 3'-UTR, a miR-34a predicted binding site on PRKD1 3'-UTR was mutated to insert a mutation sequence into a pGL3-control vector (FIG. 1C). As illustrated in FIG. 1C, miR-34a overexpression inhibited the activity of luciferase having a PRKD1 wild-type sequence, but the mutant was not inhibited in MCF-7-ADR cells. We screened the miR-34a expression level in breast cancer cell lines and the result that the miR-34a was down-regulated in MCF-7-ADR cells coincided with the result of FIG. 1A. The result indicated that the miR-34a negatively regulated the PRKD1 (see FIG. 1A).

Figure 7A:
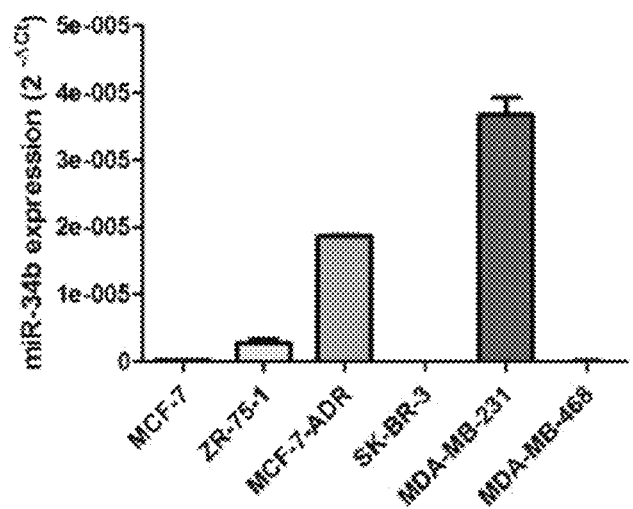
FIGS. 7A and 7B illustrate that there is no correlation between expression of miR-34b or miR-34c and expression of PRKD1.
Figure 7B:
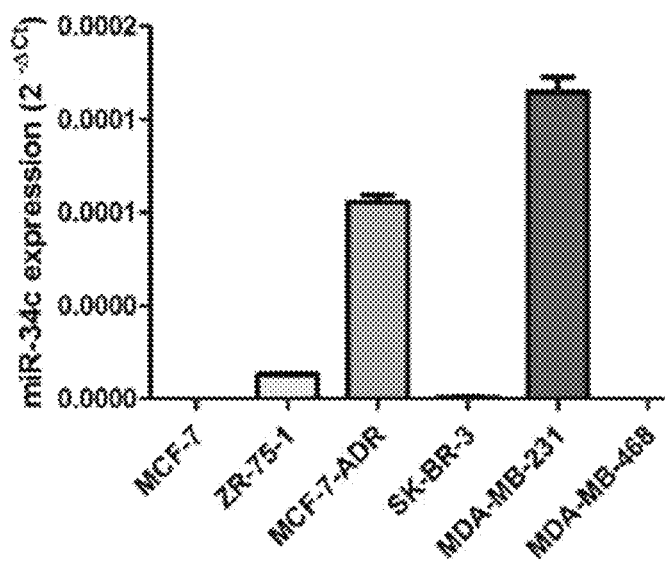

In the MCF-7-ADR cells, the expression levels of miR-34b and miR-34c were also detected, but no significant down regulation was observed (FIGS. 7A and 7B). These results indicate that the PRKD1 is down-regulated by the miR-34a in a MCF-7-ADR cell line.

Figure 2A:
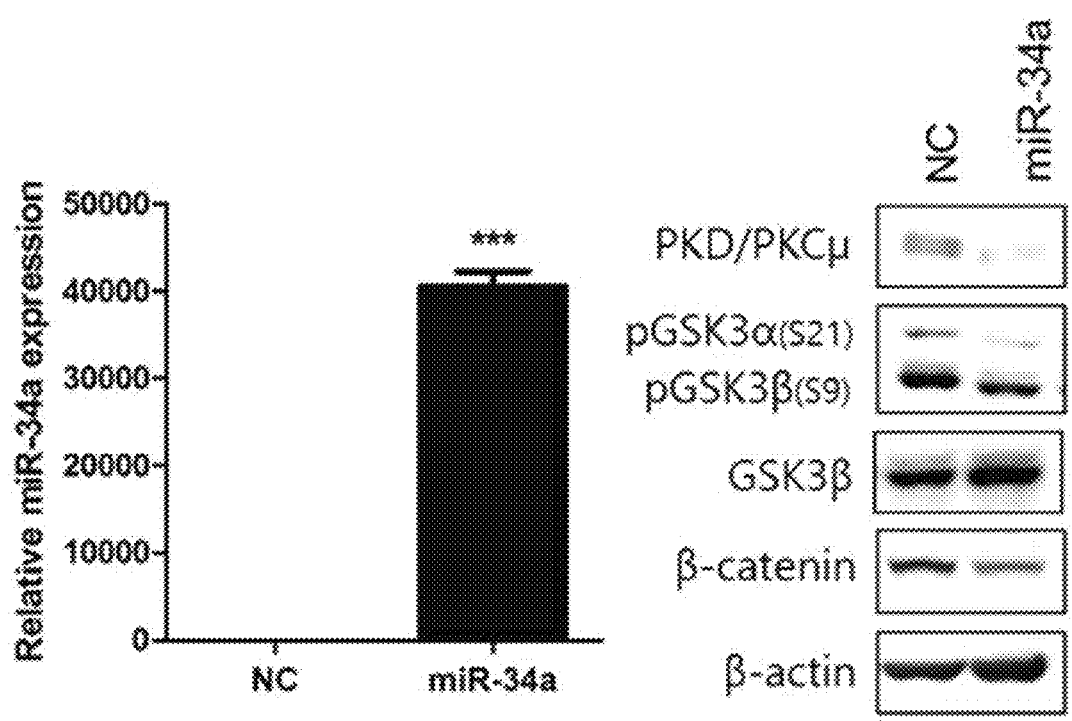
FIGS. 2A to 2E illustrate an effect of down-regulation of PKD/PKCμ on breast cancer stem cell survival rate through GSK3/β-catenin signaling in MCF-7-ADR cells. All results are obtained from at least five independent experiments.
Figure 2B:
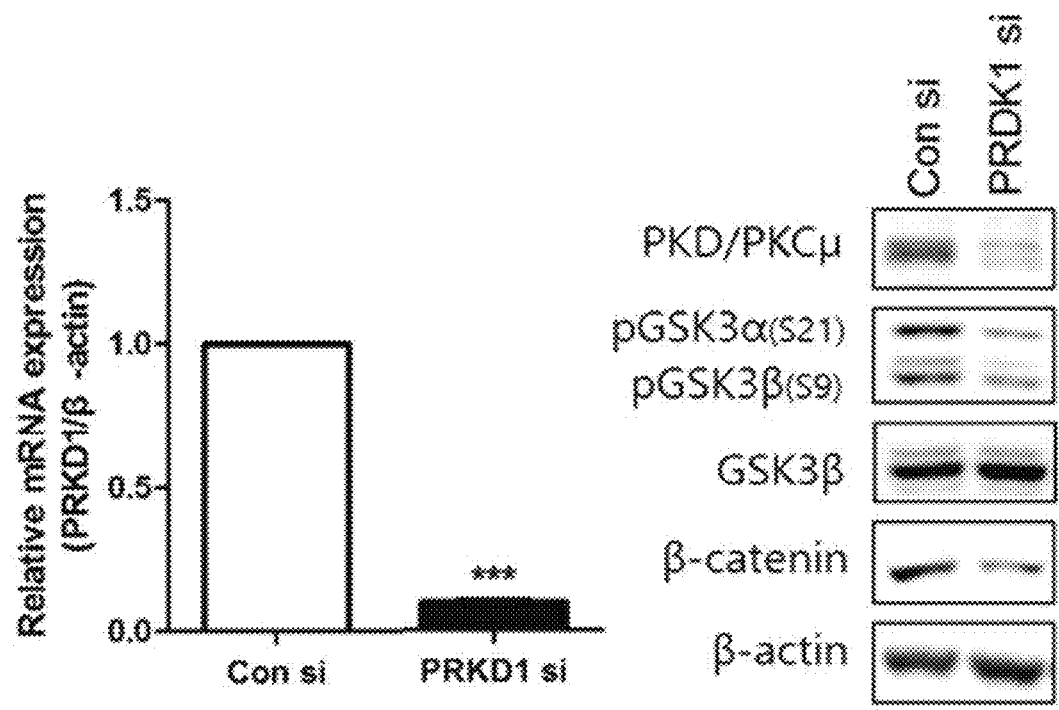
Figure 8:
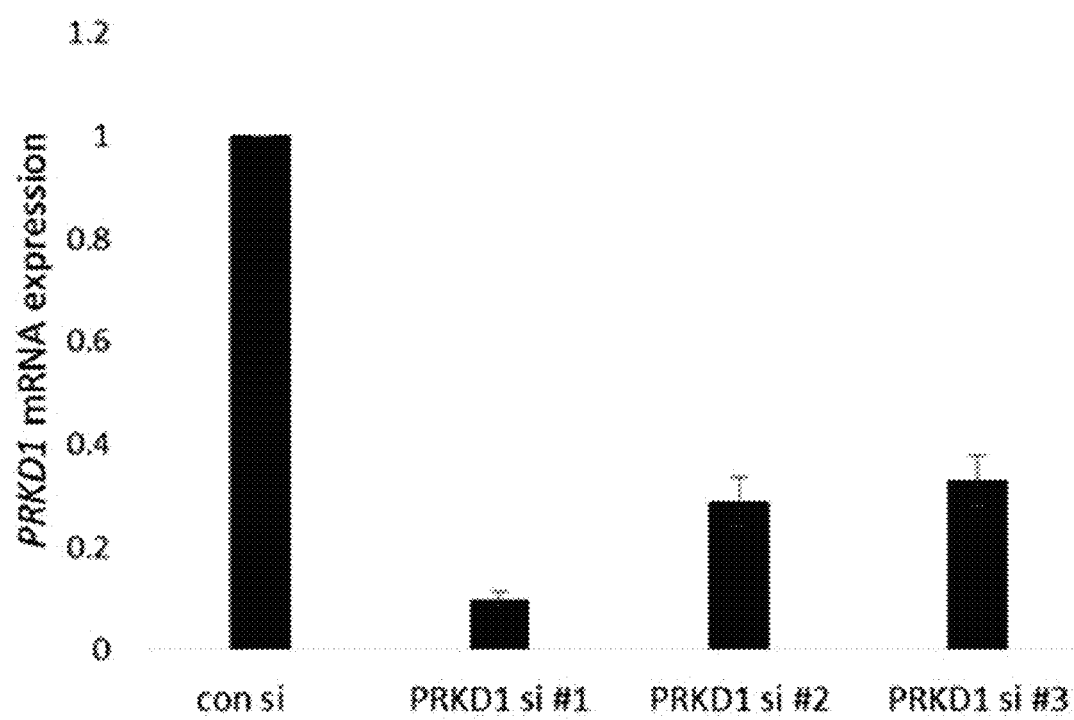
FIG. 8 illustrates comparison of efficiency of three different PRKD1 siRNAs.

Result 2: PRKD1 Promotes Breast Cancer Stemness Through GSK3/β-Catenin Signaling In order to investigate PRKD1 inhibition in tumor stem cells, MCF-7-ADR cells were transfected with a miR-34a precursor and PRKD1 siRNAs. After transfection, the expression level of miR-34a was increased and the level of PKD/PKCµ was decreased compared to a negative control (FIG. 2A). Compared with the levels observed with respect to control siRNA transfection, the expression level of PRKD1 also decreased, and this is based on the PRKD1 siRNA transfection. Interestingly, the PKD/PKCµ level also decreased according to the PRKD1 siRNA transfection (FIG. 2B). The present inventors checked the efficiency of three different PRKD1 siRNAs to exclude a nonspecific effect and selected PRKD1 siRNA #1, and the PRKD1 siRNA #1 suppressed PRKD1 better than others (FIG. 8).

Figure 9A:
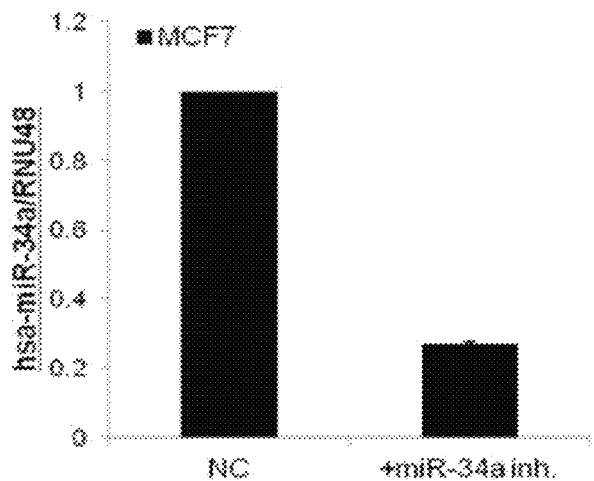
FIGS. 9A and 9B illustrate an effect of inhibited miR-34a expression in MCF-7 cells.
Figure 9B:
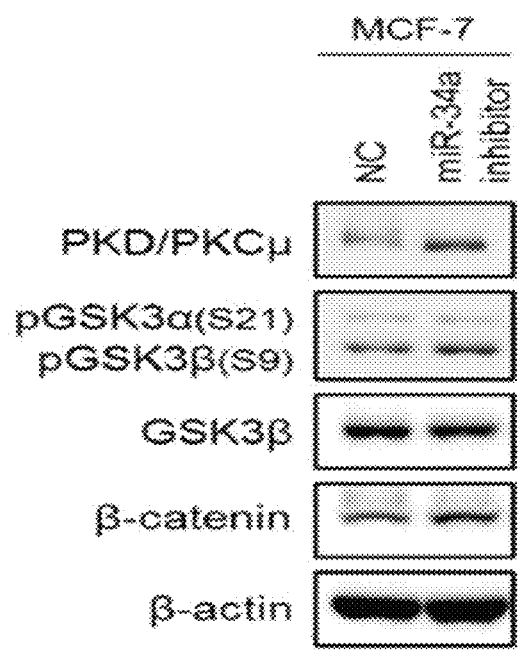

PRKD1 phosphorylation of β-catenin in Thr112/Thr120 may be crucial for cell-cell junctions in prostate cancer cells [20]. Furthermore, the complex of CDC42, PAR6 and PKCζ binds to GSK3β and catalyzes phosphorylation of Ser9 to inhibit GSK3β [21]. In order to correlate PRKD1 with GSK3/β-catenin signaling, western blot analysis was performed. The result showed that PKD/PKCµ reduction inhibited β-catenin expression and phosphorylation of GSK3α and GSKβ (FIG. 2A). These results were verified in a control and PRKD1 siRNA-treated cells (FIG. 2B). In addition, the present inventors verified that the expression level of miR-34a was decreased by changing GSK3/β-catenin signaling after transfection with miR-34a in MCF-7 cells as a control (FIGS. 9A and 9B).

Figure 2C:
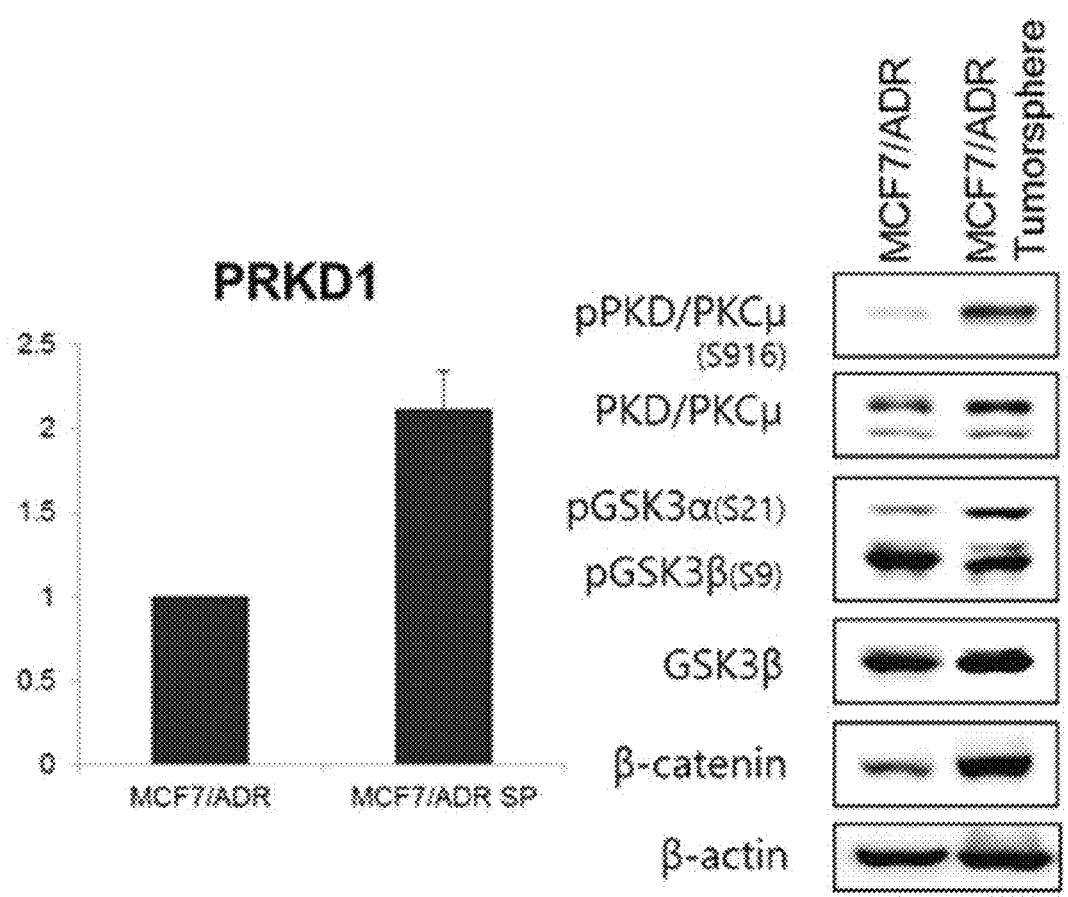
Figure 2D:
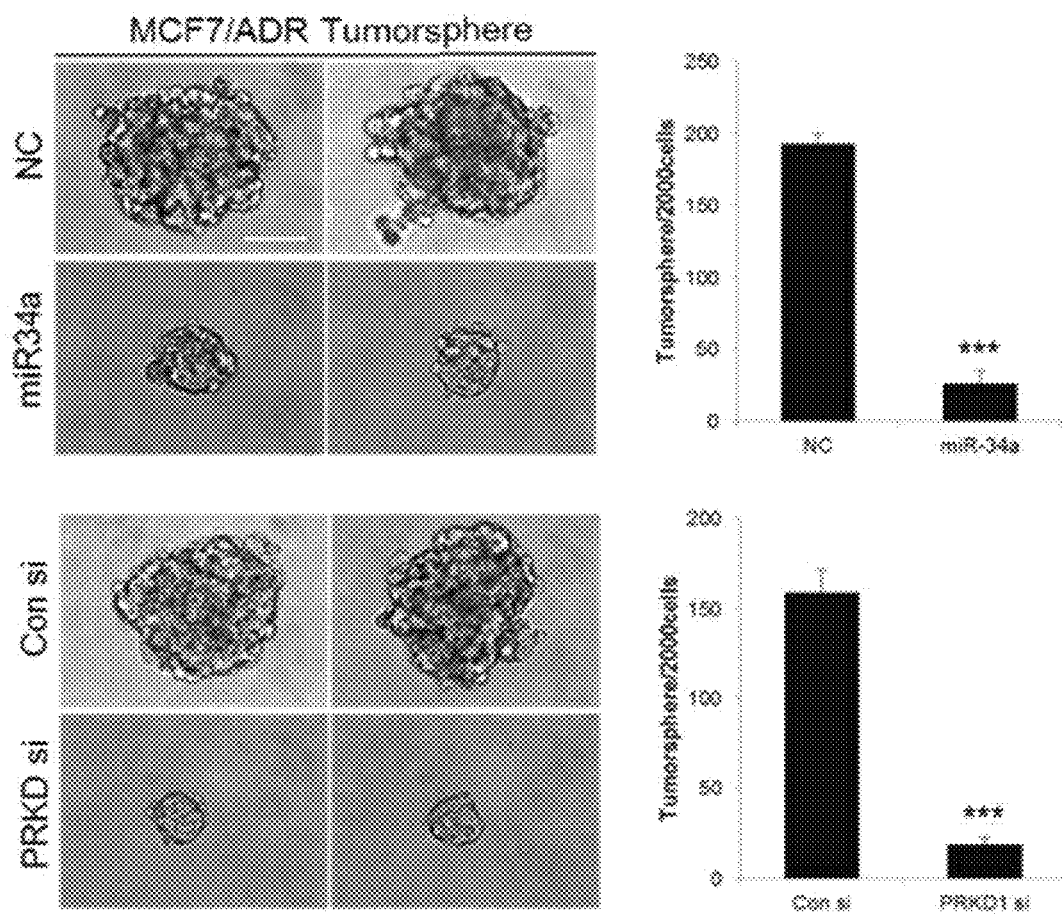
Figure 2E:
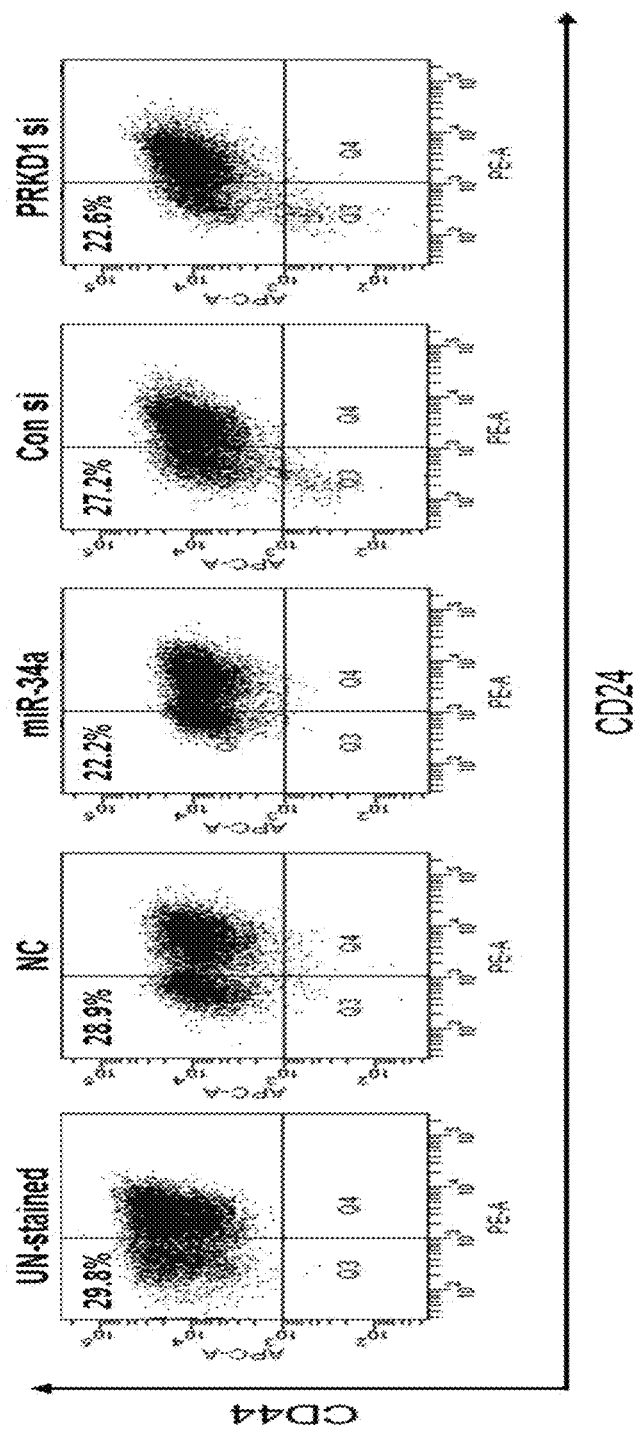
Figure 10A:
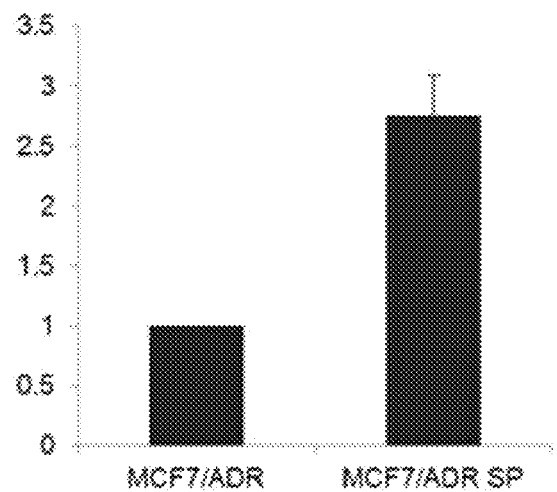
FIGS. 10A and 10B illustrate an expression level of a cancer cell stemness marker in MCF-7-ADR cells.
Figure 10B:
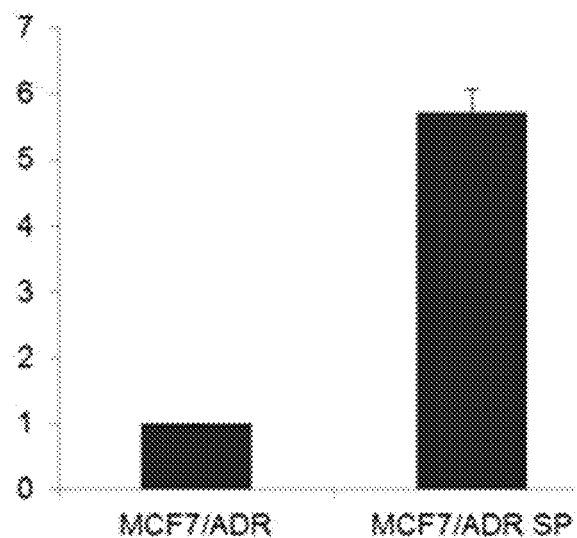
Figure 11A:
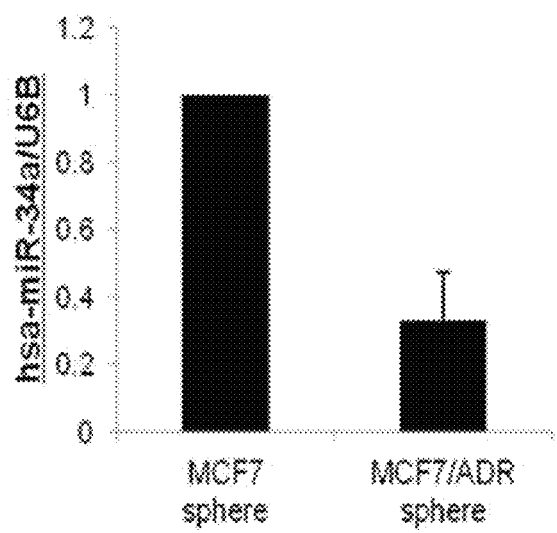
FIGS. 11A and 11B illustrate expression levels of miR-34a and PRKD1 in MCF-7 cells and MCF-7-ADR breast cancer stem cells.
Figure 11B:
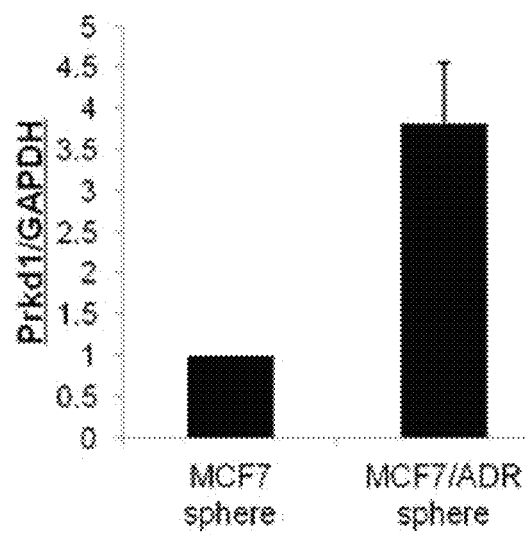

PRKD1 expression and GSK3/β-catenin signaling were up-regulated in MCF-7-ADR cells forming tumorspheres (FIG. 2C). Tumor stemness markers such as OCT4 and SOX2 were highly expressed in MCF-7-ADR cells in a tumorsphere state (FIGS. 10A and 10B). In addition, the expression of miR-34a was low and the expression of PRKD1 was high in MCF-7-ADR breast cancer stem cells compared with MCF-7 breast cancer stem cells (FIGS. 11A and 11B). In order to investigate the effect of PRKD1 knockdown on breast cancer cell stemness, a tumorsphere formation assay was performed. PRKD1 knockdown by the miR-34a precursor and PRKD1 siRNA significantly reduced the number of tumorspheres (>70 µm) compared to the control (FIG. 2D). In addition, breast cancer stem cell (BCSC) counts were stained with a breast cancer stem cell marker CD44+/CD24− and analyzed by fluorescence-activated cell classification. The number of CD44+/CD24− (Q1) was reduced by PRKD1 knockdown (FIG. 2E). In summary, the PRKD1 may regulate cancer cell stemness by changing GSK3/β-catenin signaling in MCF-7-ADR cells.

Figure 3A:
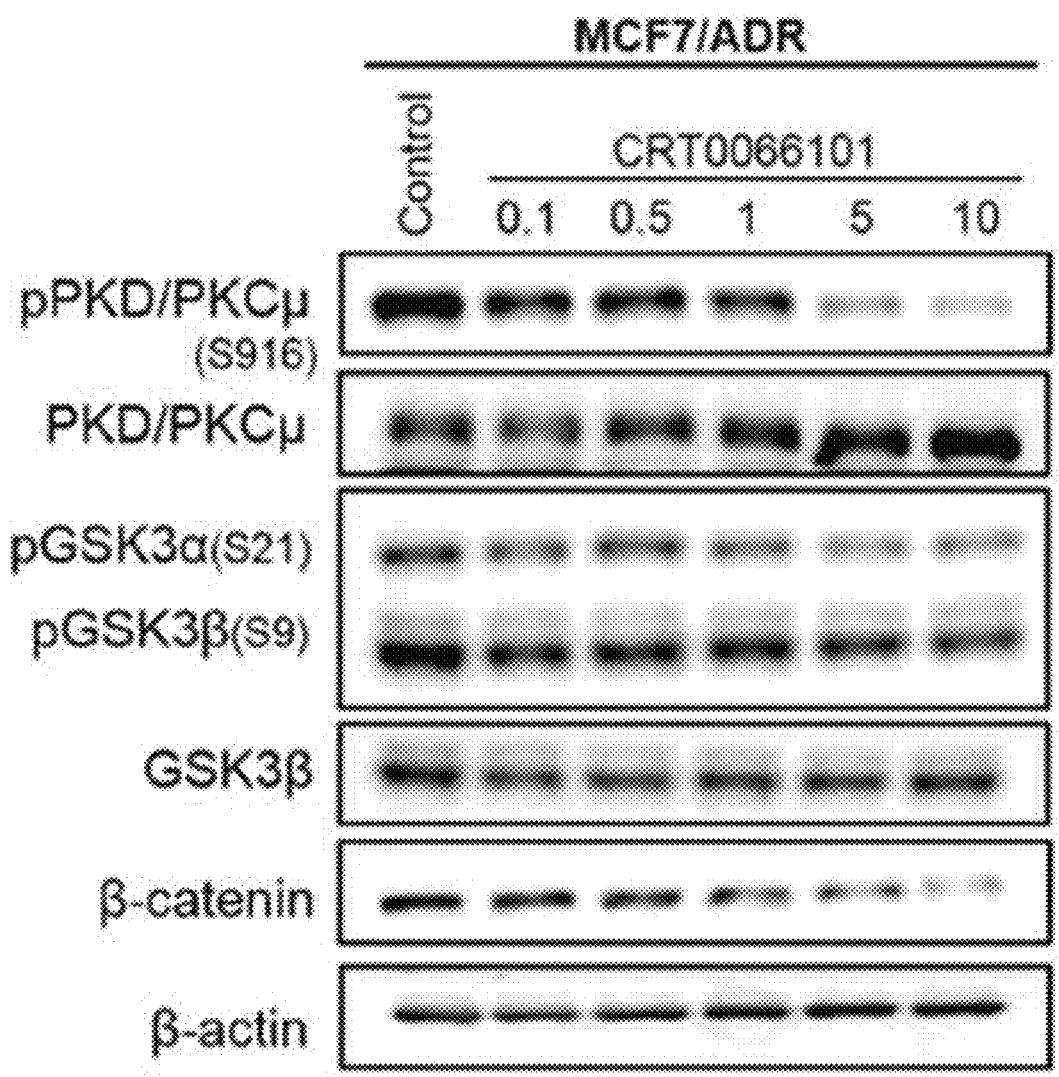
FIGS. 3A to 3C illustrate an effect of CRT0066101 on breast cancer stem cell survival rate through GSK3/β-catenin signaling in MCF-7-ADR cell line.
Figure 12A:
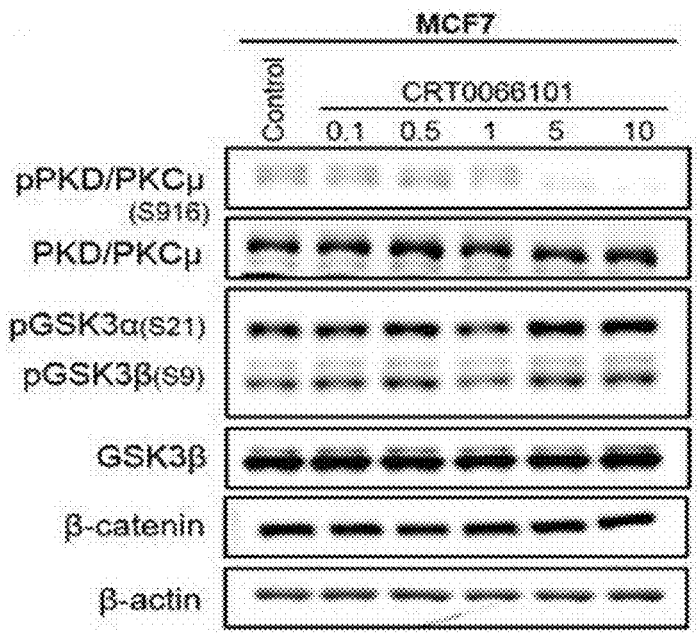
FIGS. 12A and 12B illustrate that there is no change in GSK3/β-catenin signaling and cell survival rate after treatment of CRT0066101 in MCF-7 cells.

Result 3: PKD/PKCµ Phosphorylation Inhibition Reduces Self-Renewal Capacity of Breast Cancer Stem Cells It was found that a PKD/PKCµ phosphorylation-related had two possible active pathways. One is protein kinase C (PKC)-dependent phosphorylation (Ser744/Ser748) and the other is autophosphorylation (Ser916). For sufficient activation, autophosphorylation needs to occur immediately after PKC-dependent phosphorylation [10, 11]. CRT0066101 is an inhibitor that targets PKD autophosphorylation [16]. In order to determine a role of PKD/PKCµ autophosphorylation, MCF-7-ADR cells were treated with 1 µM or 5 µM of CRT0066101. As a result of western blotting, CRT0066101 inhibited phosphorylation of PKD/PKCµ and GSK3/β-catenin in MCF-7-ADR cells (FIG. 3A). However, GSK3/β-catenin signaling in MCF-7 cells was not affected by treatment of CRT0066101 (FIG. 12A).

Figure 3B:
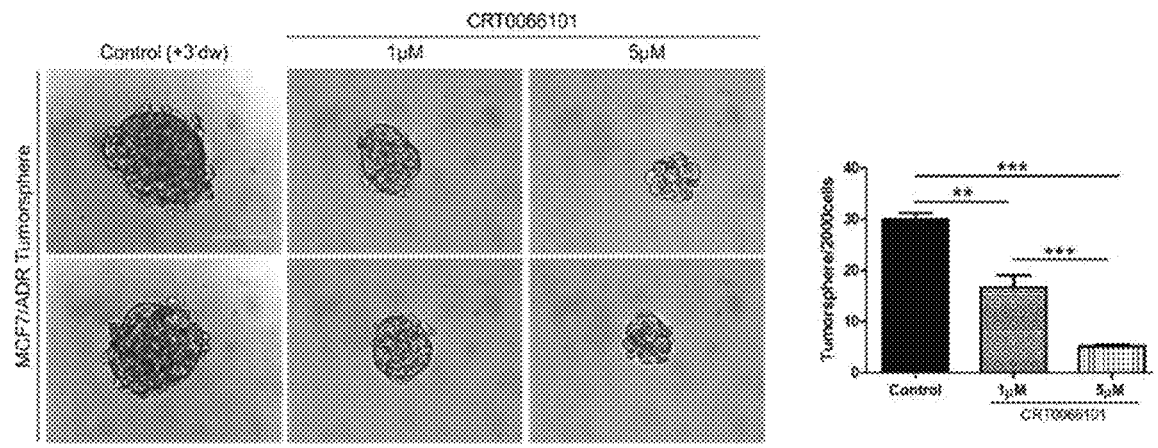
Figure 3C:
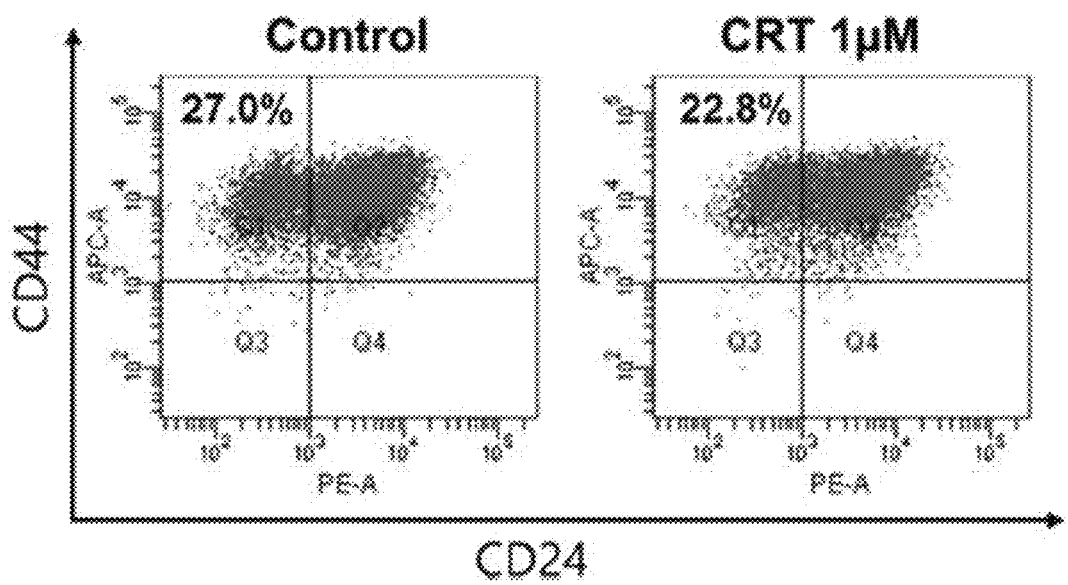

The number of tumorspheres (>70 μm) after treatment of CRT0066101 (1 μM or 5 μM) decreased dose-dependently compared to the control (FIG. 3B). As expected, the number (Q1) of CD44+/CD24− also decreased after treatment with 1 μM CRT0066101 (FIG. 3C). These results indicate that PKD/PKCμ autophosphorylation through GSK3/β-catenin signaling is required for the regulation of breast cancer cell stemness.

Result 4: PRKD1 Restores Drug Resistance

Figure 4A:
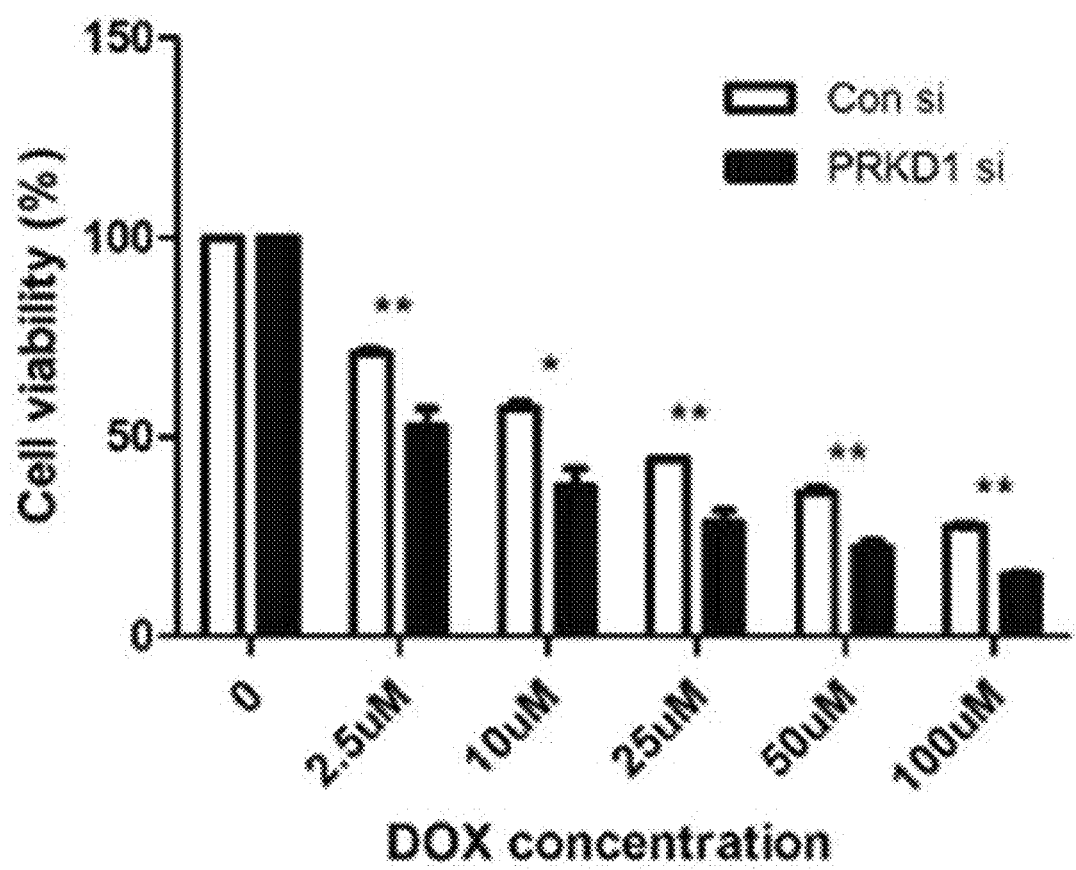
FIGS. 4A to 4E illustrate inhibitory effects of PKCμ on MCF-&-ADR cell apoptosis.
Figure 4B:
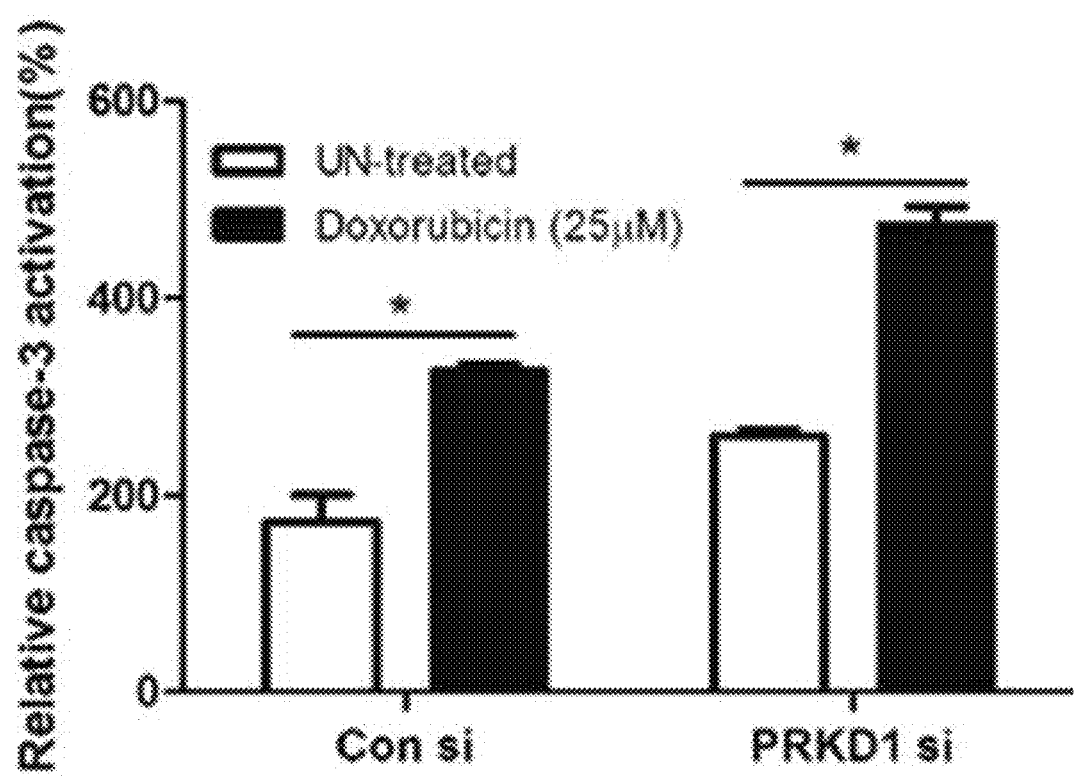
Figure 4C:
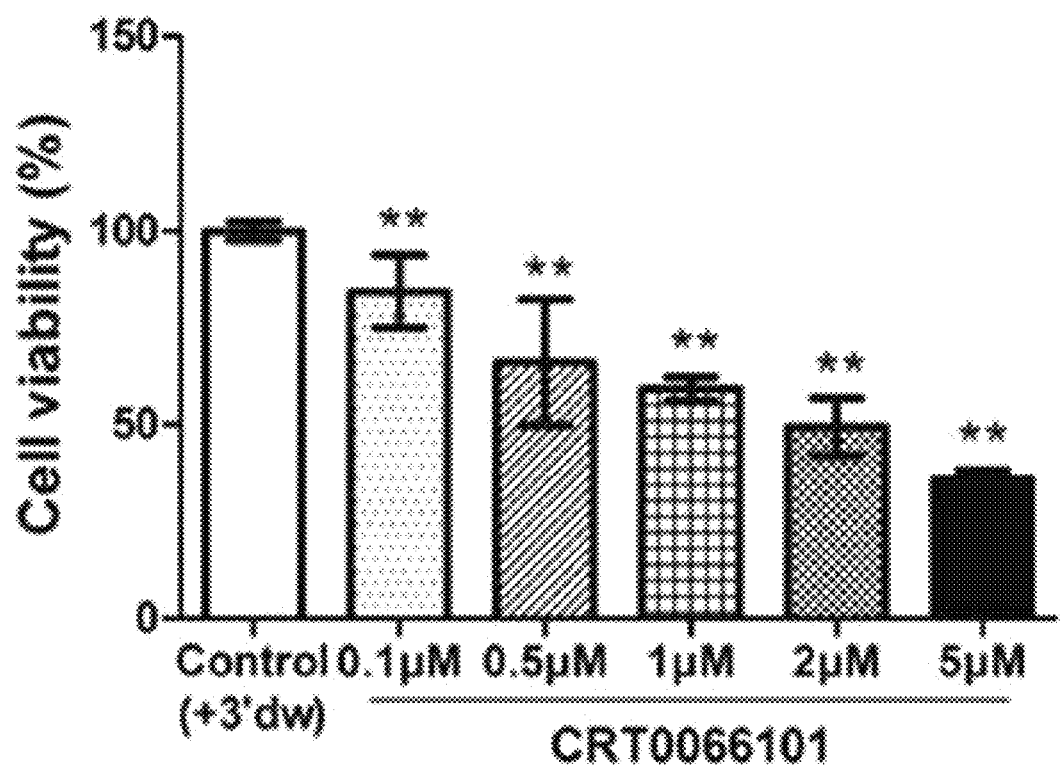
Figure 4D:
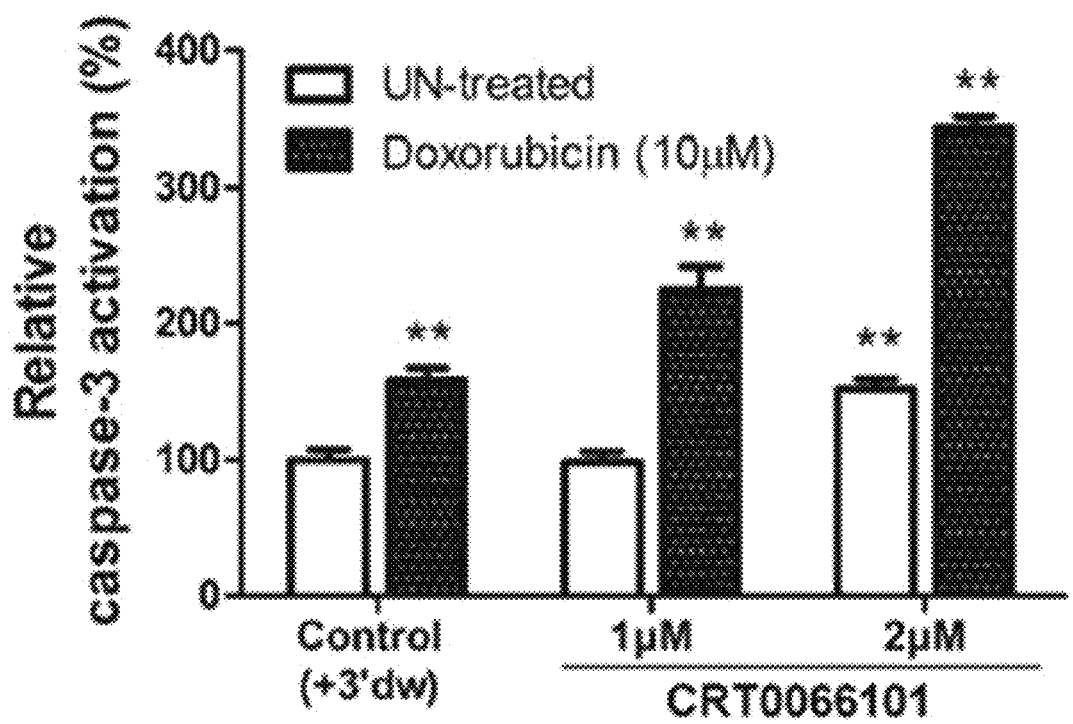
Figure 4E:
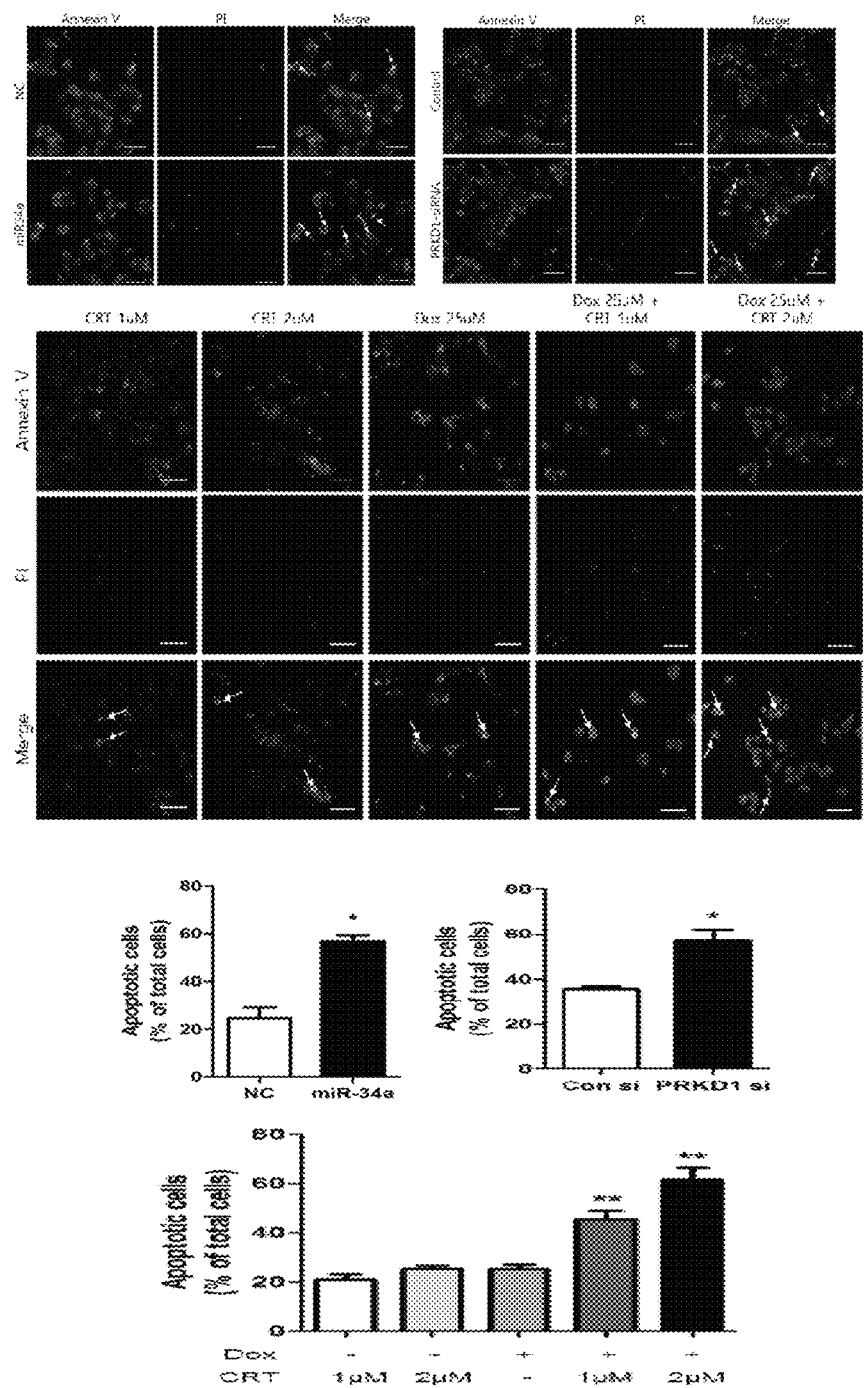
Figure 12B:
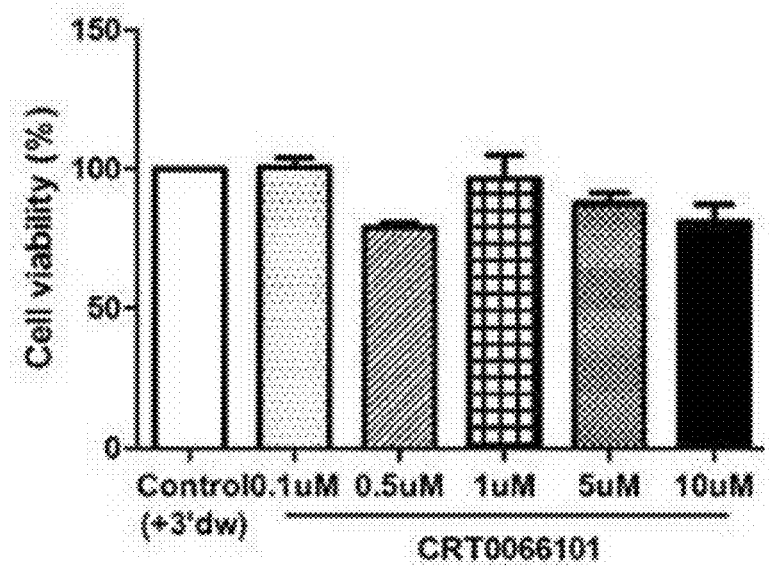

As above study results, it was reported that PKD/PKCμ is associated with apoptosis through caspase-3 inhibition [22]. Therefore, the present inventors examined whether PRKD1 inhibition activated apoptosis in MCF-7-ADR cells. As a result, it was found that the reduction reaction further occurred in beast cancer stem cells. As illustrated in FIG. 4A, when MCF-7-ADR cells were exposed to doxorubicin (DOX), cell survival rate was reduced dose-dependently. Significantly, PRKD1 knockdown more increased an apoptosis level compared to the control. In order to determine whether the decrease in cell survival rate was due to apoptosis, caspase-3 activation was measured. As a result of inhibiting PRKD1, higher caspase-3 activity was shown than the control. In addition, when the PRKD1 was knockdown after doxorubicin treatment, caspase-3 activity was increased compared to the doxorubicin-treated control (FIG. 4B). Further, inhibition of PRKD1 by treatment with 0.1 to 5 μM CRT0066101 in MCF-7-ADR cells decreased cell survival rate dose-dependently (FIG. 4C), but cell survival rate did not decrease in MCF-7 cells as compared to CRT0066101 treatment (FIG. 12B). When combining CRT0066101-treatment with doxorubicin-induced apoptosis, cell survival rate is significantly lowered as compared with treatment of CRT0066101 alone (FIG. 4D). Further, we also performed Annexin V and propidium iodide (PI) staining to verify that PRKD1 knockdown or PKD/PKCμ phosphorylation inhibition increase apoptosis. As a result, it was verified that the initiation of apoptosis in miR-34a precursor treated cells, PRKD1 siRNA treated cells and doxorubicin treated cells was increased compared to the control. Interestingly, when CRT0066101 was treated in the doxorubicin-treated cells, the level of apoptosis increased (FIG. 4E). In summary, these data indicate that PRKD1 down regulation or inhibition of PKD/PKCμ autophosphorylation restore drug resistance in MCF-7-ADR cells.

Figure 5A:
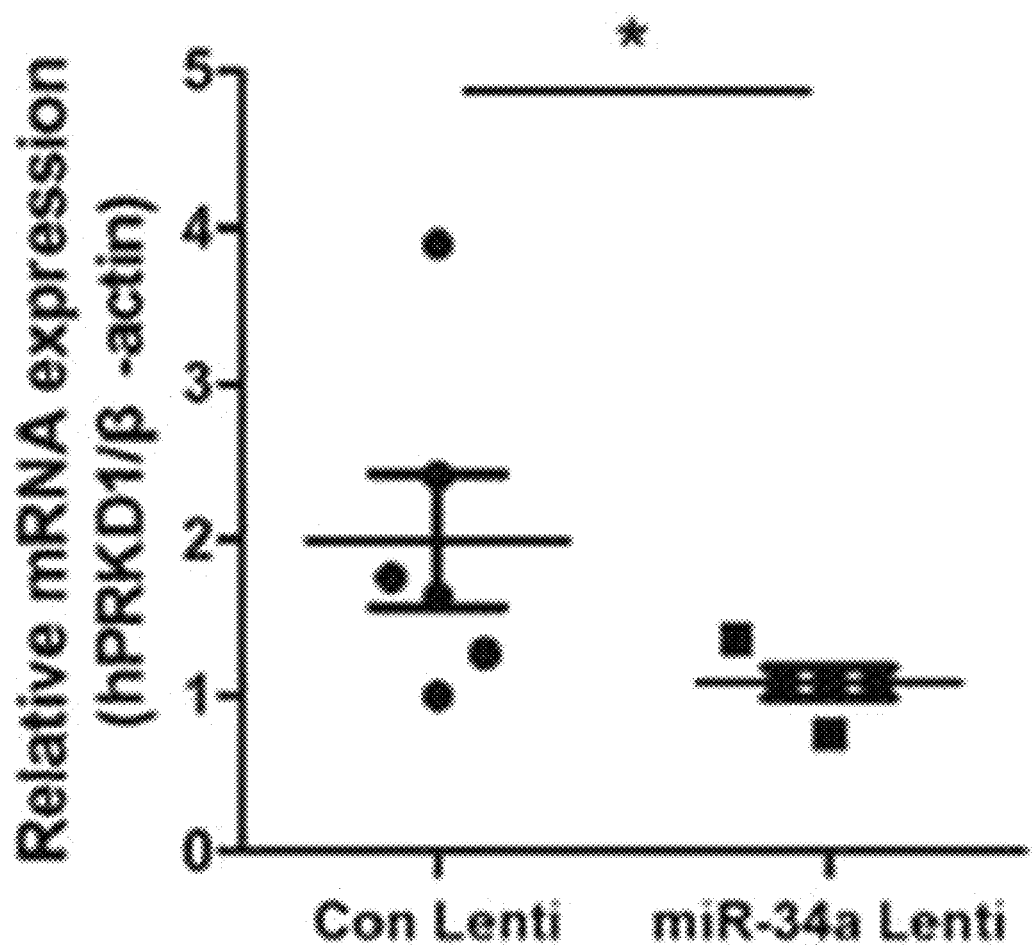
FIGS. 5A to 5G illustrate that in a xenograft model, down-regulation of PKCμ inhibits formation of tumor.
Figure 5B:
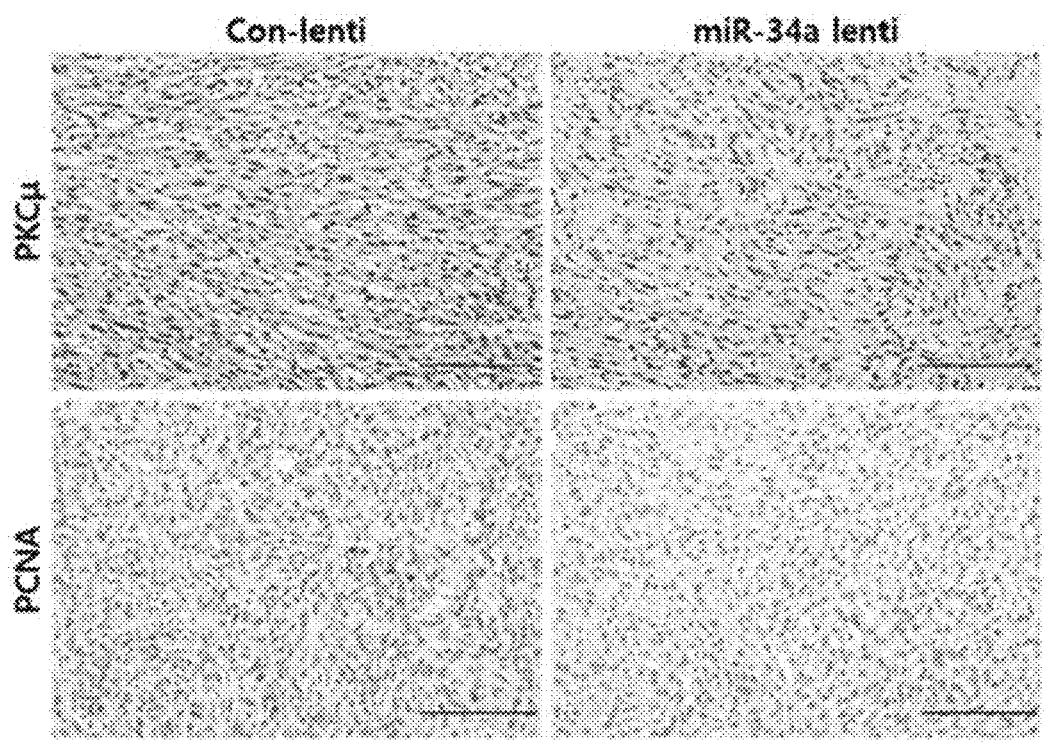
Figure 5C:
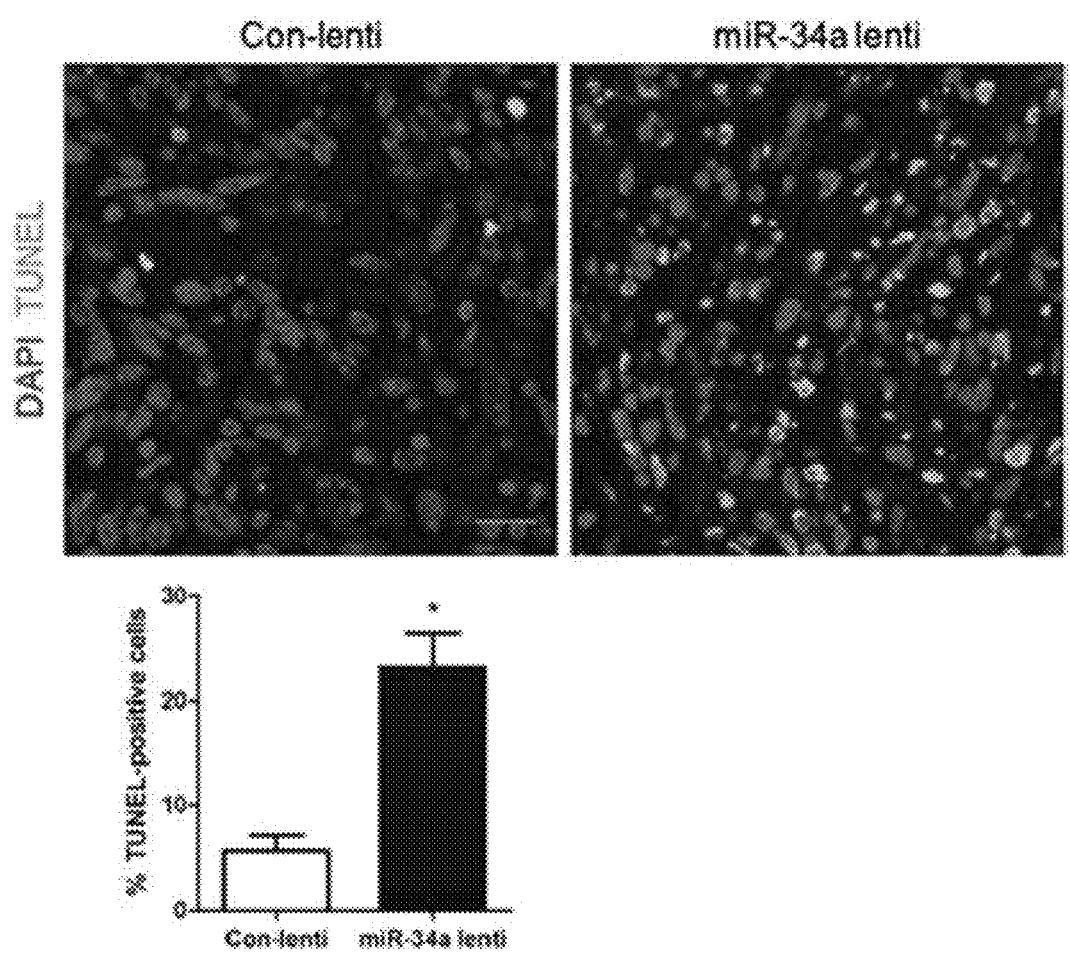

Result 5: in the Xenograft Model, Inhibition or Down-Regulation of PKCμ Function Inhibits Tumor Growth In preceding studies of the present inventors, the present inventors verified that miR-34a inhibits NOTCH1 expression in nude mice to inhibit tumor formation [5]. In the present invention, whether the down-regulation of PRKD1 by miR-34a inhibits tumor growth in the xenograft model has been studied. The expression level of PRKD1 was down-regulated in miR-34a overexpressed tumor compared to the control tumor (FIG. 5A). As a result of immunohistochemistry (IHC) staining, PKCμ and a proliferating cell nuclear antigen (PCNA) decreased in miR-34a overexpressed tumor (FIG. 5B). In order to determine whether PRKD1 inhibition by miR-34a inhibits tumor growth through apoptosis, the present inventors performed terminal deoxynucleotidyl transferase dUTP nick-end labeling (TUNEL) assay. As a result, miR-34a overexpressed tumor possessed more apoptotic cells than the control tumor (FIG. 5C).

Figure 5D:
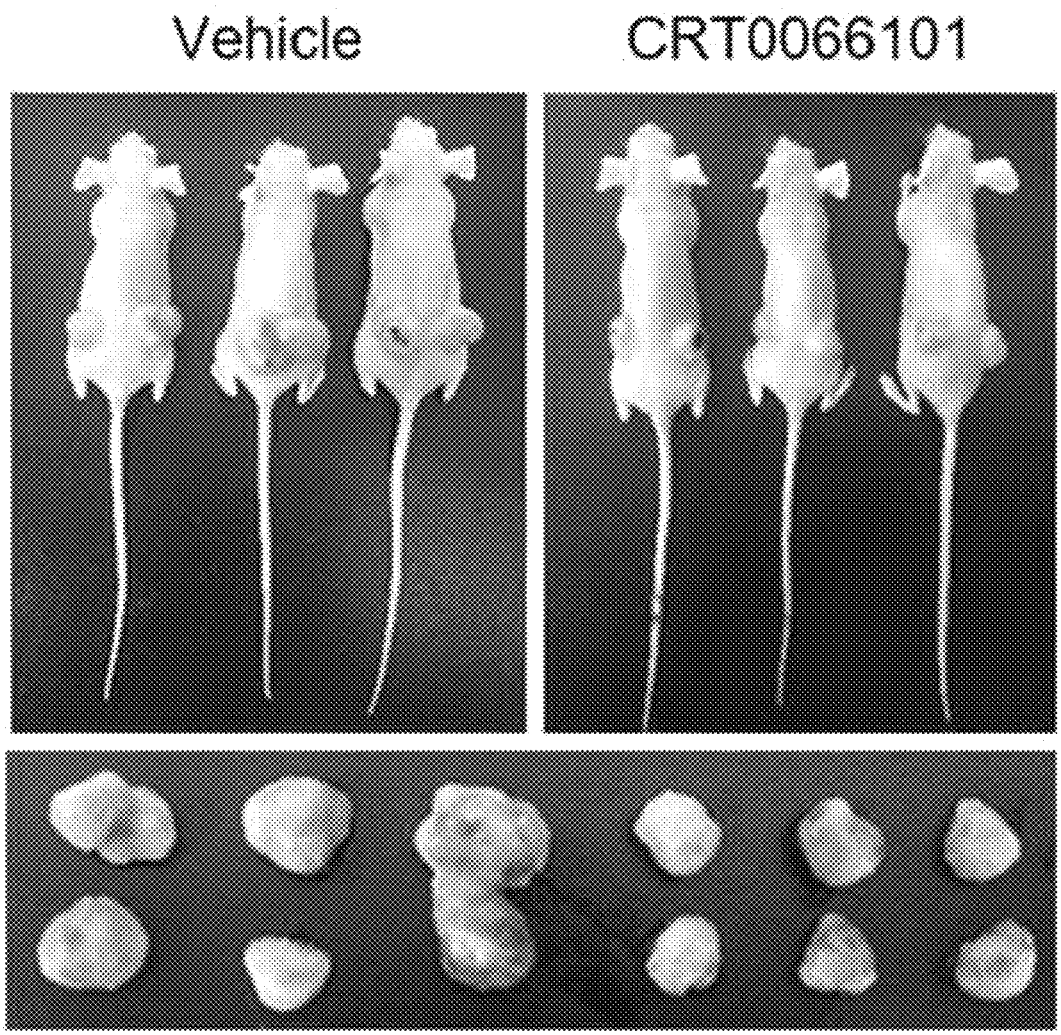
Figure 5E:
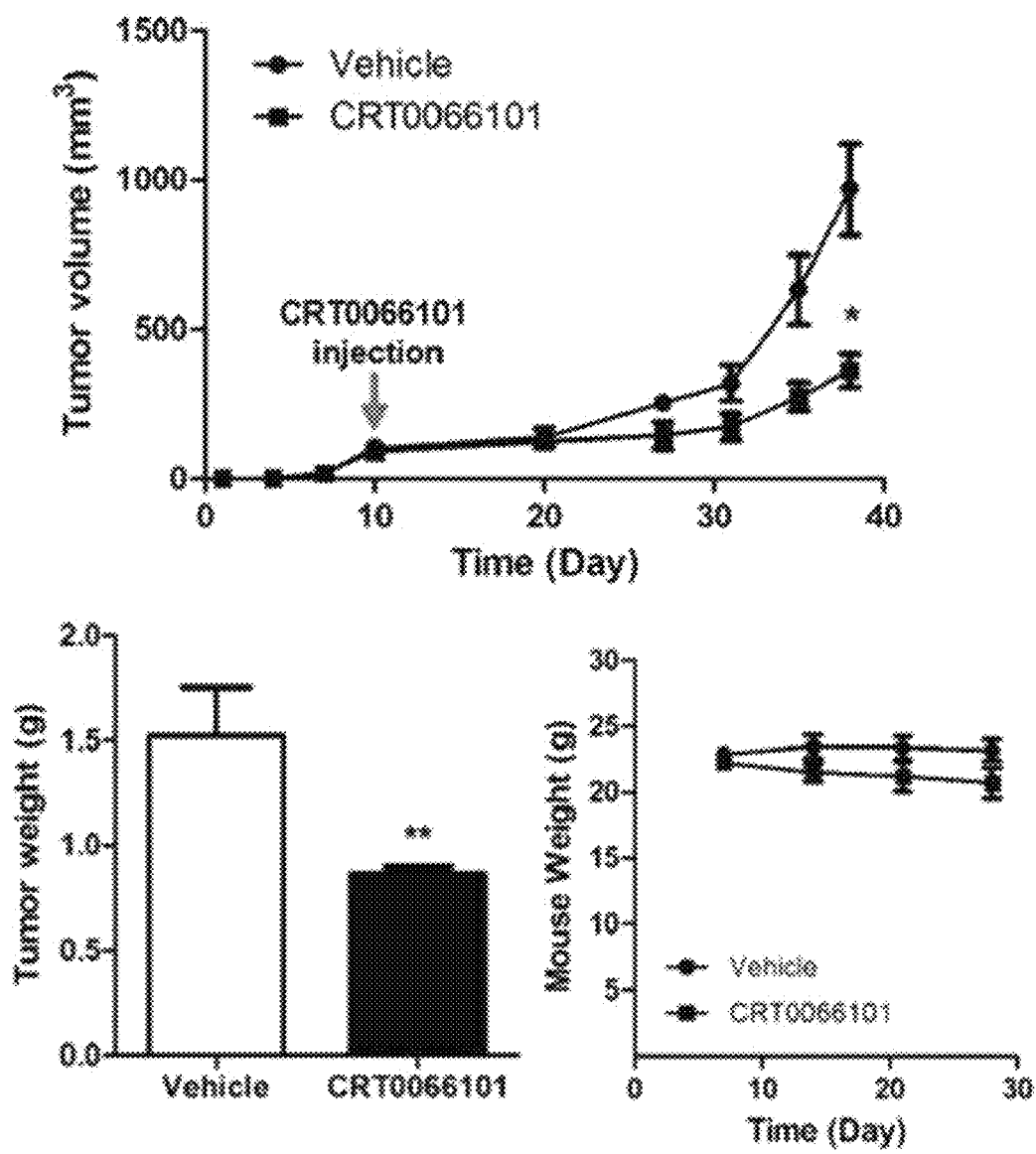
Figure 5F:
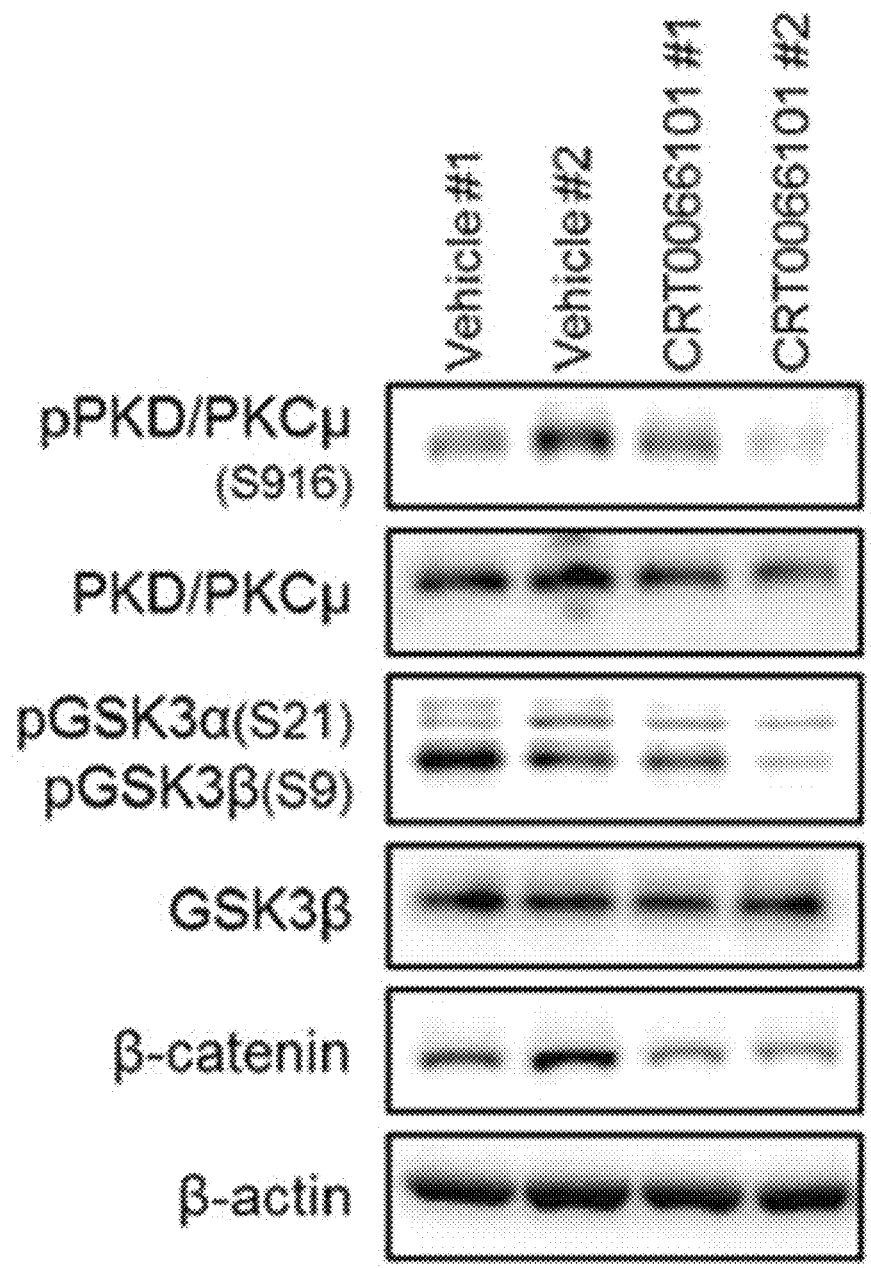
Figure 5G:
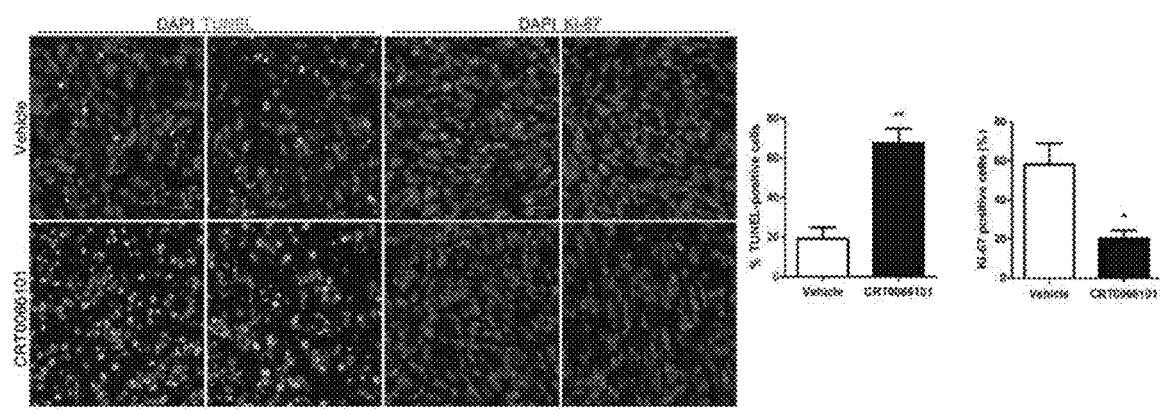

In order to further evaluate the inhibitory effect of PKD/PKCμ, mice having tumor xenografted and established with MCF-7-ADR cells were treated with 65 mg/kg of CRT0066101 daily for 4 weeks. The tumor size in the CRT0066101-treated mice was reduced compared to the untreated control (FIG. 5D). As expected, the tumor weight of CRT0066101-treated mice was reduced compared to the control tumor. The CRT0066101 treatment in all animals did not cause side effects such as significant sign of toxicity and weight loss (FIG. 5E). In addition, the down regulation of phosphorylated PKD/PKCμ through GSK3/β-catenin signaling was also verified by western blot analysis (FIG. 5F). Finally, the present inventors performed TUNEL analysis and Ki-67 staining to verify whether CRT0066101 enhances apoptosis and inhibits proliferation. As a result, in the CRT0066101-treated tumor, apoptosis increased and proliferation decreased as compared with the control (FIG. 5G). In conclusion, PKCμ inhibition by miR-34a or CRT0066101 plays a role in reducing tumor growth through initiation of apoptosis in vivo.

Figure 13A:
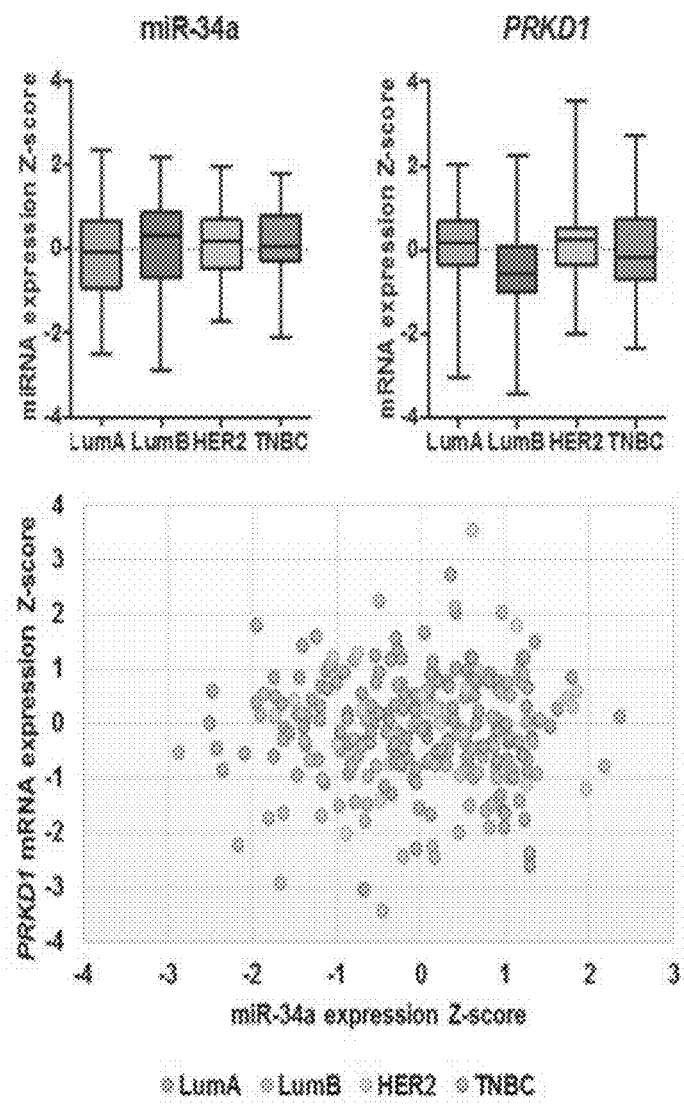
FIGS. 13A and 13B illustrate a correlation between improved PRKD1 expression and poor prognosis in a breast cancer patient.
Figure 13B:
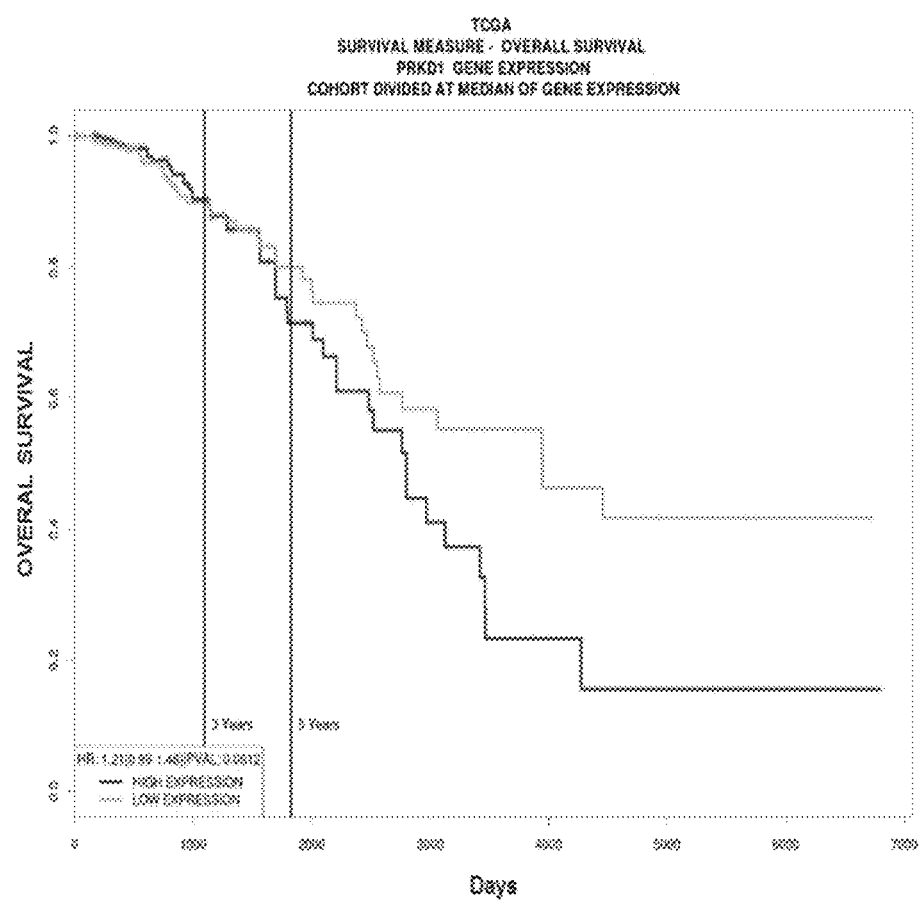

The PRKD1 is involved in cell proliferation, apoptosis, cell junction, invasion and vesicle trafficking [23]. Interestingly, PRKD1 expression has a different pattern in various tumor cells and performs dual functions as a tumor cell or tumor inhibitor [24]. The PRKD1 expression is down-regulated in invasive human breast cancer compared with a normal breast tissue [25]. Similar expression patterns were verified in microarray analysis and invasive cell models such as SK-BR-3, T-47D and MDA-MB-231 [25 and 26]. Furthermore, when PRKD1 promoter methylation is returned, invasion and metastasis of breast cancer cells are blocked [27]. The experimental results of the present inventors show that the PRKD1 expression patterns in a MCF-7-ADR cell line increase drug resistance. The PRKD1 was highly expressed in a drug resistant cell line including doxorubicin-resistant MCF-7-ADR cells, tamoxifen-resistant LCC2 cells, and tamoxifen and fluvestrant-resistant LCC9 cells. Accordingly, we concluded that PRKD1 expression is associated with drug resistance. The present inventors studied expression of miR-34a and PRKD1 in a TCGA data set (FIG. 13A). Since the PRKD1 was highly expressed in drug-resistant breast cancer cells, the present inventors could not find an inverse correlation between expression of miR-34a and expression of PRKD1 in the TCGA database. The present inventors further verified the overall survival rate according to a PRKD1 expression level in the TCGA clinical data set (FIG. 13B). This graph shows that the survival rate of patients with high expression of PRKD1 is lower than that of patients with low expression of PRKD1. Although the inverse correlation between expression of miR-34a and expression of PRKD1 was not verified in whole breast cancer samples, a relationship between PRKD1 expression and breast cancer patients with poor prognosis was derived. In addition, we verified that the down-regulated PRKD1 changed the apoptotic signal. Thus, it is proposed that the PRKD1 may be selected to restore drug sensitivity in breast cancer cells.

The miRNA miR-34a plays an important role in tumor inhibition. In conventional studies, it has been reported that miR-34a inhibits tumor stem cells in various tumors including prostate cancer [28], pancreatic cancer [29], medulloblastomas [30] and glioblastomas [31]. This molecule also inhibits tumor cell survival, tumor stemness, metastasis, and chemical resistance while inhibiting targets associated with cell cycle, differentiation, and apoptosis [17]. In the present invention, it was verified that miR-34a negatively regulates the PRKD1 in MCF-7-ADR cells. In addition, the PRKD1 is a new target of miR-34a and found that the miR-34a binds to PRKD1 3'-UTR. Furthermore, the present inventors have found that miR-34a-PRKD1 interaction plays an important role in overcoming tumor stemness and drug resistance in a breast cancer cell line. In the preceding studies, it was reported that the PRKD1 phosphorylates β-catenin at Thr112/Thr120 and overexpression of PRKD1 inhibits β-catenin-mediated transcriptional activity [32]. β-catenin phosphorylation occurs through GSK3, and the GSK3 targets β-catenin as a part of a Wnt-signaling protein complex [33]. In addition, GSK3β is a kinase that is involved in prostate cancer cellization and migration through a Wnt-independent mechanism [34]. In the present invention, it has been observed that the reduced PRKD1 inhibits the self-renewal capacity of breast cancer stem cells through the modification of GSK3/β-catenin signaling. Therefore, these results indicate that the PRKD1 activates breast cancer stemness through GSK3/β-catenin signaling.

Harikumar and the like discovered CRT0066101 as an inhibitor specific to all PKD isoforms [16] and found that the CRT0066101 blocked growth of pancreatic cancer by inhibiting PRKD1 autophosphorylation [16]. The present inventors blocked PRKD1 activation by treating breast cancer cell lines and xenograft models with CRT0066101. This result indicates that CRT0066101 may be a potential therapeutic agent for breast cancer patients.

Figure 6:
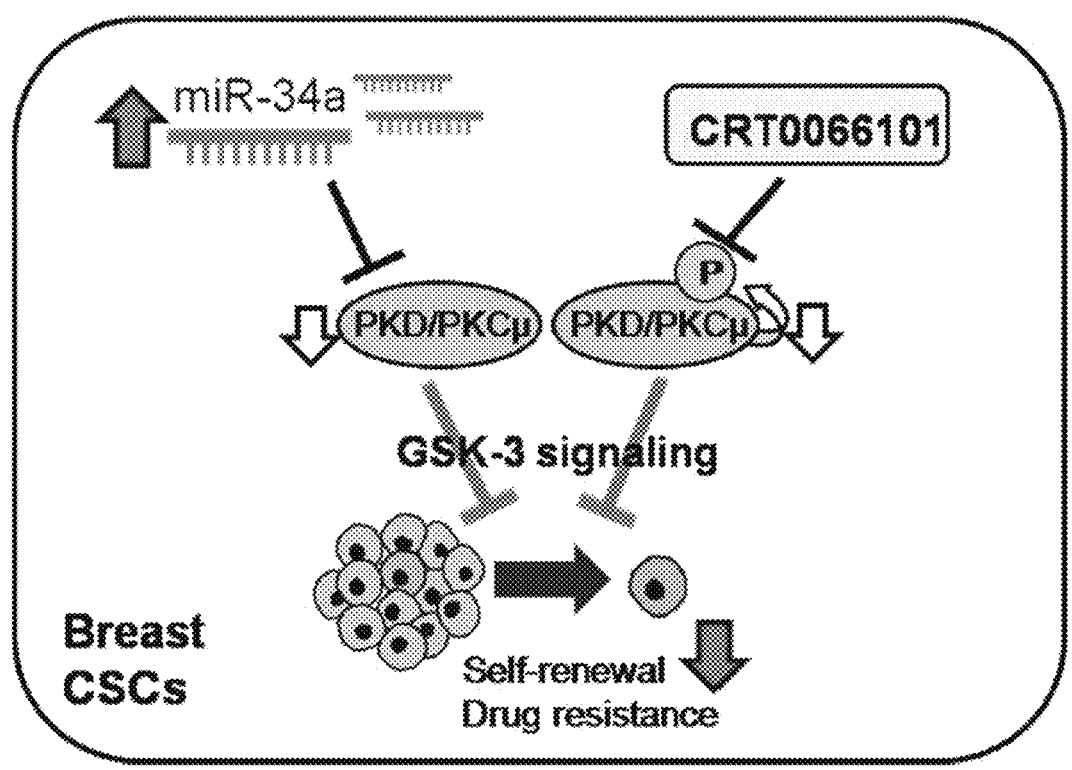
FIG. 6 illustrates the hypothesis of the present invention. The miR-34a directly inhibits PRKD1 and the CRT0066101 inhibits self-phosphorylated PKD/PKCμ. Two directions represent different regulations of self-renewal capacity in breast cancer stem cells and drug resistance in MCF-7-ADR cells through GSK3/β-catenin signaling.

In the present invention, PRKD1 overexpression in the MCF-7-ADR cell line had a negative correlation with miR-34a overexpression. The present inventors found that miR-34a binds to PRKD1 3'-UTR to inhibit cancer cell stemness in breast cancer stem cells through the GSK3/β-catenin signaling pathway. Furthermore, the present inventors found that CRT0066101, known as the PRKD1 inhibitor, affects the reduction of breast cancer stem cells and drug resistance through the GSK3/β-catenin signaling pathway (FIG. 6). In addition, we observed that ectopic expression of miR-34a and CRT0066101 treatment inhibited cancer growth in a xenograft model. In conclusion, the PRKD1 was negatively regulated by miR-34a to inhibit cancer cell stemness and drug resistance in breast cancer cell lines. These results indicate that the PRKD1 is a major molecule that activates breast cancer stemness and drug resistance and promotes the activation as a potential therapeutic target in breast cancer.

The invention claimed is:

1. A method of inhibiting the growth of anticancer drug-resistant breast cancer stem cells, comprising administering an effective amount of a protein kinase D1 expression or activity inhibitor as an active ingredient to a subject having cancer.

2. The method of inhibiting the growth of anticancer drug-resistant breast cancer stem cells of claim 1, wherein the protein kinase D1 has an amino acid sequence of SEQ ID NO: 1.

3. The method of inhibiting the growth of anticancer drug-resistant breast cancer stem cells of claim 1, wherein the protein kinase D1 expression inhibitor is any one selected from the group consisting of an antisense nucleotide complementarily binding to mRNA of a protein kinase D1 gene, a short interfering RNA, a short hairpin RNA, and miR-34a.

4. The method of inhibiting the growth of anticancer drug-resistant breast cancer stem cells of claim 1, wherein the protein kinase D1 activity inhibitor is any one selected from the group consisting of compounds that specifically bind to the protein kinase D1, peptides, peptide mimetics, aptamers, antibodies and CRT0066101.

5. The method of inhibiting the growth of anticancer drug-resistant breast cancer stem cells of claim 1, wherein the cancer is selected by cancer stem cell markers CD44+ and CD24.

6. The method of inhibiting the growth of anticancer drug-resistant breast cancer stem cells of claim 1, wherein the protein kinase D1 expression or activity inhibitor inhibits expression of β-catenin and phosphorylation of GSK3α and GSKβ.

7. A method of treating anticancer drug-resistant breast cancer, comprising administering an effective amount of a protein kinase D1 expression or activity inhibitor, and antitumor agent as active ingredients to a subject having cancer.

8. The method of treating anticancer drug-resistant breast cancer of claim 7, wherein the protein kinase D1 has an amino acid sequence of SEQ ID NO: 1.

9. A method for measuring expression or activity of protein kinase D1 for providing information of anticancer drug-resistant breast cancer prognosis, the method comprising a step of measuring expression or activity of protein kinase D1 in cells or tissues isolated from a subject.

* * * * *